US011759660B2

(12) United States Patent
Han et al.

(10) Patent No.: US 11,759,660 B2
(45) Date of Patent: Sep. 19, 2023

(54) SYSTEMS AND METHODS FOR RECONSTRUCTING FLUENCE MAP

(71) Applicant: SHANGHAI UNITED IMAGING HEALTHCARE CO., LTD., Shanghai (CN)

(72) Inventors: Huajie Han, Shanghai (CN); Shiquan Zhang, Shanghai (CN); Yanfang Liu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 323 days.

(21) Appl. No.: 17/084,709

(22) Filed: Oct. 30, 2020

(65) Prior Publication Data
US 2021/0187326 A1    Jun. 24, 2021

(30) Foreign Application Priority Data

Dec. 18, 2019 (CN) .......................... 201911314184.8

(51) Int. Cl.
*A61N 5/10* (2006.01)

(52) U.S. Cl.
CPC ......... *A61N 5/1071* (2013.01); *A61N 5/1045* (2013.01); *A61N 5/1047* (2013.01); *A61N 2005/1072* (2013.01)

(58) Field of Classification Search
CPC .. A61N 5/1071; A61N 5/1045; A61N 5/1047; A61N 5/103; A61N 2005/1072
See application file for complete search history.

(56) References Cited

U.S. PATENT DOCUMENTS 9,550,076 B2 *  1/2017  Han ....................... G06T 5/003
2004/0165696 A1  8/2004  Lee
(Continued)

FOREIGN PATENT DOCUMENTS

CN    104117151 A  * 10/2014
CN    104117151 A    10/2014
(Continued)

OTHER PUBLICATIONS

The Second Office Action in Chinese Application No. 201911314184.8 dated Aug. 16, 2021, 15 pages.
(Continued)

*Primary Examiner* — Thaddeus B Cox
*Assistant Examiner* — Marc D. Honrath
(74) *Attorney, Agent, or Firm* — METIS IP LLC

(57) ABSTRACT

The present disclosure relates to systems and methods for reconstructing fluence map. The system may obtain a plurality of radiation tasks based on a radiotherapy plan. Each of the plurality of radiation tasks may include a radiation field corresponding to the radiation task. For each of the plurality of radiation tasks, the system may determine whether a shape change between a radiation field corresponding to the radiation task and a radiation field corresponding to a preceding radiation task exceeds a shape change threshold. The system may determine a fluence map corresponding to the radiation task based on a first determination result of whether the shape change between the radiation field corresponding to the radiation task and the radiation field corresponding to the preceding radiation task exceeds the shape change threshold.

20 Claims, 12 Drawing Sheets

(56) References Cited

U.S. PATENT DOCUMENTS

| | | |
|---|---|---|
| 2006/0259282 A1 | 11/2006 | Failla et al. |
| 2007/0145295 A1 | 6/2007 | Banine et al. |
| 2013/0034211 A1* | 2/2013 | Claesson .............. A61N 5/1045 378/65 |
| 2017/0232274 A1 | 8/2017 | Isola et al. |
| 2018/0345042 A1* | 12/2018 | Voronenko ........... A61N 5/1045 |
| 2020/0203022 A1 | 6/2020 | Li |
| 2020/0353287 A1 | 11/2020 | Maltz |

FOREIGN PATENT DOCUMENTS

| | | | |
|---|---|---|---|
| CN | 105413068 A | | 3/2016 |
| CN | 107545137 A | | 1/2018 |
| CN | 107961447 A | | 4/2018 |
| CN | 104866928 B | * | 8/2018 |
| CN | 109513121 A | | 3/2019 |

OTHER PUBLICATIONS

Guo, Caiping, Study of the Methods for Improving the Quality and Efficiency of Intensity Modulated Radiotherapy Plan, China Excellent Doctoral Dissertation Full-text Database (Ph.D.) Medical and Health Science and Technology Series, 2018, 147 pages.

"Radiation Therapy", Web page <http://www.yixue.com/%E6%94%BE%E7%96%97#1.E3.80.81.E5.87.8F.E5.B0.91.E5.8F.97.E7.85.A7.E5.89.82.E9.87.8F>, Jan. 26, 2014.

First Office Action in Chinese Application No. 201911314184.8 dated Mar. 8, 2021, 10 pages.

* cited by examiner

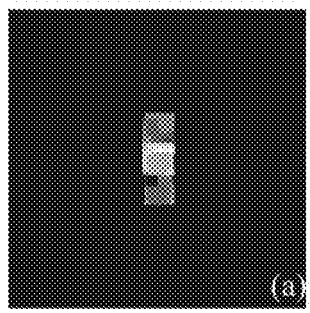
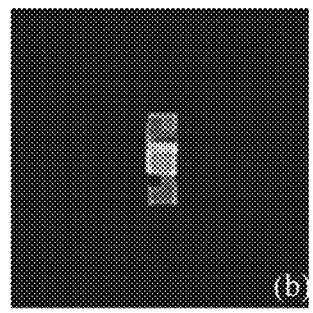
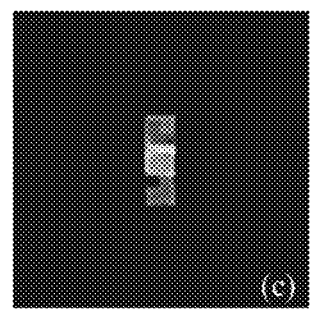
FIG. 10A　　　　　　　FIG. 10B　　　　　　　FIG. 10C
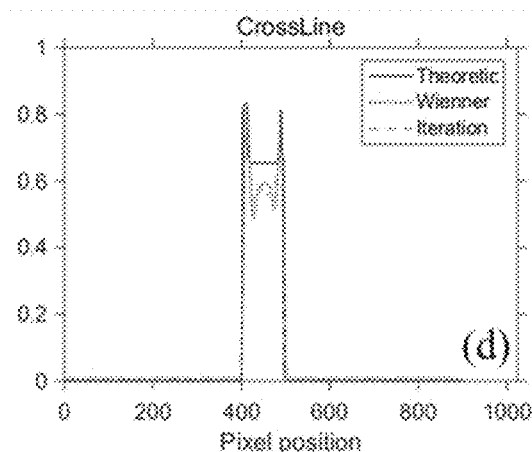
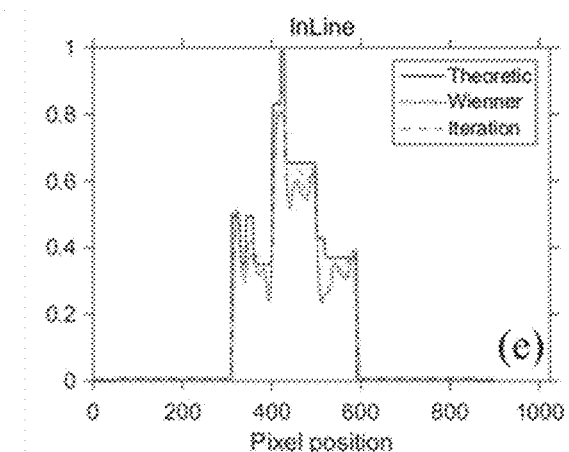
FIG. 10D　　　　　　　　　　　FIG. 10E

SYSTEMS AND METHODS FOR RECONSTRUCTING FLUENCE MAP

CROSS-REFERENCE TO RELATED APPLICATIONS

This application claims priority to Chinese Patent Application No. 201911314184.8 filed on Dec. 18, 2019, the contents of which are incorporated herein by reference.

TECHNICAL FIELD

The present disclosure generally relates to radiotherapy, and more particularly, to systems and methods for reconstructing a fluence map in radiotherapy.

BACKGROUND

Radiotherapy (RT) is widely used in clinical treatment for cancers and other conditions. During a radiotherapy treatment, an actual dose of radiation passing through a target region (e.g., a tumor region) and/or normal tissue of an object (e.g., a patient) has a great influence on the clinical treatment effect. Therefore, it is desirable to provide systems and methods for reconstructing a fluence map that can reflect the actual dose of radiation passing through the target region and/or normal tissue.

SUMMARY

An aspect of the present disclosure relates to a system for reconstructing a fluence map. The system may include at least one storage device including a set of instructions and at least one processor configured to communicate with the at least one storage device. When executing the set of instructions, the at least one processor is configured to direct the system to perform operations. The operations may include obtaining a plurality of radiation tasks based on the radiotherapy plan. Each of the plurality of radiation tasks may include a radiation field corresponding to the radiation task. The operations may include, for each of the plurality of radiation tasks, determining whether a shape change between a radiation field corresponding to the radiation task and a radiation field corresponding to a preceding radiation task exceeds a shape change threshold. The operations may further include determining a fluence map corresponding to the radiation task based on a first determination result of whether the shape change between the radiation field corresponding to the radiation task and the radiation field corresponding to the preceding radiation task exceeds the shape change threshold.

In some embodiments, the first determination result may include that the shape change exceeds the shape change threshold. The determining the fluence map corresponding to the radiation task based on the first determination result may include updating the fluence map corresponding to the radiation task.

In some embodiments, the updating the fluence map corresponding to the radiation task may include determining whether a movement change of the radiation field corresponding to the radiation task during an execution process of the radiation task exceeds a movement change threshold, and determining the fluence map corresponding to the radiation task based on a second determination result of whether the movement change of the radiation field corresponding to the radiation task exceeds the movement change threshold.

In some embodiments, the second determination result may include that the movement change exceeds the movement change threshold. The determining the fluence map corresponding to the radiation task based on the second determination result may include determining a plurality of radiation sub-tasks based on the movement change threshold and determining the fluence map corresponding to the radiation task based on the plurality of radiation sub-tasks.

In some embodiments, a change of radiation sub-fields corresponding to two neighboring radiation sub-tasks may be within the movement change threshold. For each of the plurality of radiation sub-tasks, a change of a radiation sub-field corresponding to the radiation sub-task during an execution process of the radiation sub-task may be within the movement change threshold.

In some embodiments, the determining the fluence map corresponding to the radiation task based on the plurality of radiation sub-tasks may include, for each of the plurality of radiation sub-tasks, determining a fluence sub-map corresponding to the radiation sub-task; and determining the fluence map corresponding to the radiation task by combining a plurality of fluence sub-maps corresponding to the plurality of radiation sub-tasks.

In some embodiments, for each of the plurality of radiation sub-tasks, the determining the fluence sub-map corresponding to the radiation sub-task may include obtaining an electronic portal imaging device (EPID) image corresponding to the radiation sub-task and determining the fluence sub-map corresponding to the radiation sub-task based on the EPID image corresponding to the radiation sub-task.

In some embodiments, the updating the fluence map corresponding to the radiation task may include obtaining an EPID image corresponding to the radiation task and determining the fluence map corresponding to the radiation task by converting the EPID image corresponding to the radiation task.

In some embodiments, the first determination result may include that the shape change is less than the shape change threshold. The determining the fluence map corresponding to the radiation task based on the first determination result may include designating a fluence map corresponding to the preceding radiation task as the fluence map corresponding to the radiation task.

In some embodiments, the operations may further include determining a target fluence map by combining a plurality of fluence maps corresponding to the plurality of radiation tasks.

In some embodiments, the radiation field may be formed by a plurality of leaves or jaw baffles of a collimator at different positions. The shape change may include a movement of at least one of the plurality of leaves or jaw baffles.

A further aspect of the present disclosure relates to a system for reconstructing a fluence map. The system may include at least one storage device including a set of instructions and at least one processor configured to communicate with the at least one storage device. When executing the set of instructions, the at least one processor is configured to direct the system to perform operations. The operations may include obtaining a plurality of radiation tasks based on a radiotherapy plan. Each of the plurality of radiation tasks may include a radiation field corresponding to the radiation task. The operations may include, for each of the plurality of radiation tasks, determining whether a movement change of the radiation field corresponding to the radiation task during an execution process of the radiation task exceeds a movement change threshold. The operations may further include determining a fluence map corresponding to the radiation task based on a second determination result of whether the movement change of the radiation field corresponding to the radiation task exceeds the movement change threshold.

In some embodiments, the second determination result may include that the movement change exceeds the movement change threshold. The determining the fluence map corresponding to the radiation task based on the second determination result may include determining a plurality of radiation sub-tasks based on the movement change threshold and determining the fluence map corresponding to the radiation task based on the plurality of radiation sub-tasks.

In some embodiments, a change of radiation sub-fields corresponding to two neighboring radiation sub-tasks may be within the movement change threshold. For each of the plurality of radiation sub-tasks, a change of a radiation sub-field corresponding to the radiation sub-task during an execution process of the radiation sub-task may be within the movement change threshold.

In some embodiments, the determining the fluence map corresponding to the radiation task based on the plurality of radiation sub-tasks may include for each of the plurality of radiation sub-tasks, determining a fluence sub-map corresponding to the radiation sub-task, and determining the fluence map corresponding to the radiation task by combining a plurality of fluence sub-maps corresponding to the plurality of radiation sub-tasks.

In some embodiments, for each of the plurality of radiation sub-tasks, the determining the fluence sub-map corresponding to the radiation sub-task may include obtaining an electronic portal imaging device (EPID) image corresponding to the radiation sub-task and determining the fluence sub-map corresponding to the radiation sub-task based on the EPID image corresponding to the radiation sub-task.

A still further aspect of the present disclosure relates to a method for reconstructing a fluence map. The method may be implemented on a computing device including at least one processor and at least one storage device. The method may include obtaining a plurality of radiation tasks based on a radiotherapy plan. Each of the plurality of radiation tasks may include a radiation field corresponding to the radiation task. The method may include for each of the plurality of radiation tasks, determining whether a shape change between a radiation field corresponding to the radiation task and a radiation field corresponding to a preceding radiation task exceeds a shape change threshold. The method may further include determining a fluence map corresponding to the radiation task based on a first determination result of whether the shape change between the radiation field corresponding to the radiation task and the radiation field corresponding to the preceding radiation task exceeds the shape change threshold.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 10A is a schematic diagram illustrating an ideal fluence image;

FIG. 10B is a schematic diagram illustrating a fluence image reconstructed based on a Wiener filter deconvolution;

FIG. 10O is a schematic diagram illustrating a fluence image reconstructed based on an iterative deconvolution;

FIG. 10D is a schematic diagram illustrating horizontal numerical comparison curves corresponding to fluence images in the FIGS. 10A-10C;

FIG. 10E is a schematic diagram illustrating longitudinal numerical comparison curves corresponding to fluence images in the FIGS. 10A-10C;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
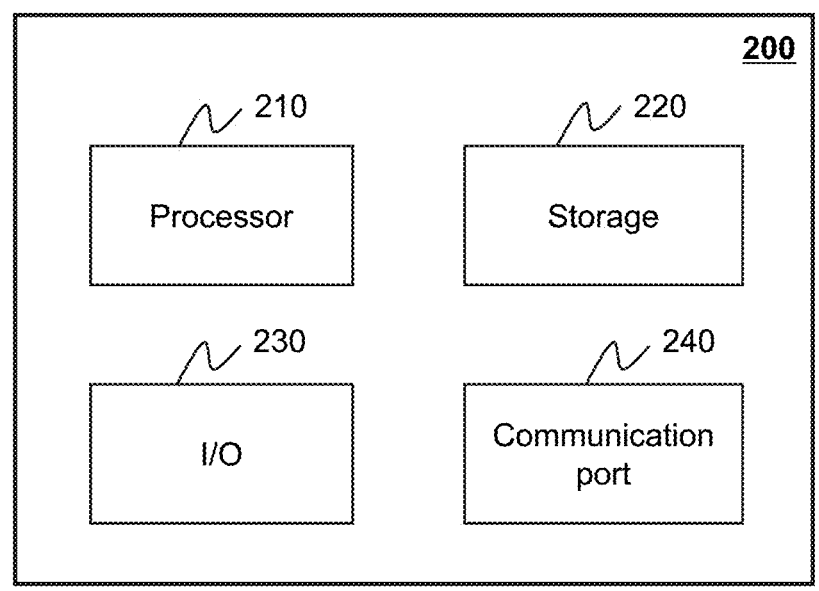
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "anatomical structure" in the present disclosure may refer to gas (e.g., air), liquid (e.g., water), solid (e.g., stone), cell, tissue, organ of an object, or any combination thereof, which may be displayed in an image (e.g., a second image, or a first image, etc.) and really exist in or on the object's body. The term "region," "location," and "region" in the present disclosure may refer to a location of an anatomical structure shown in the image or an actual location of the anatomical structure existing in or on the object's body, since the image may indicate the actual location of a certain anatomical structure existing in or on the object's body.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

Provided herein are systems and methods for non-invasive biomedical imaging/treatment, such as for disease diagnostic, disease therapy, or research purposes. In some embodiments, the systems may include an imaging system. The imaging system may include a single modality system and/or a multi-modality system. The term "modality" used herein broadly refers to an imaging or treatment method or technology that gathers, generates, processes, and/or analyzes imaging information of an object or treatments the object. The single modality system may include, for example, an ultrasound imaging system, an X-ray imaging system, a computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near-infrared spectroscopy (NIRS) imaging system, or the like, or any combination thereof. The multi-modality system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a positron emission tomography-magnetic resonance imaging (PET-MR) system, a digital subtraction angiography-magnetic resonance imaging (DSA-MRI) system, etc. In some embodiments, the medical system may include a treatment system. The treatment system may include a treatment plan system (TPS), image-guide radiotherapy (IGRT), etc. The image-guide radiotherapy (IGRT) may include a treatment device and an imaging device. The treatment device may include a linear accelerator, a cyclotron, a synchrotron, etc., configured to perform radiotherapy on a object. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc. It should be noted that the medical system described below is merely provided for illustration purposes, and not intended to limit the scope of the present disclosure.

An aspect of the present disclosure provides systems and methods for reconstructing a fluence map for radiotherapy. The systems and methods may obtain a radiotherapy plan and further obtain a plurality of radiation tasks based on the radiotherapy plan. Each of the plurality of radiation tasks may include a radiation field corresponding to the radiation task. For each of the plurality of radiation tasks, the systems and methods may determine whether a shape change between a radiation field corresponding to the radiation task and a radiation field corresponding to a preceding radiation task exceeds a shape change threshold. The systems and methods may determine a fluence map corresponding to the radiation task based on a first determination result of whether the shape change between the radiation field corresponding to the radiation task and the radiation field corresponding to the preceding radiation task exceeds the shape change threshold. The first determination result may include that the shape change exceeds the shape change threshold and the shape change is less than the shape change threshold. When the shape change exceeds the shape change threshold, the systems and methods may update the fluence map corresponding to the radiation task. When the shape change is less than the shape change threshold, the systems and methods may designate a fluence map corresponding to the preceding radiation task as the fluence map corresponding to the radiation task. Further, the systems and methods may determine a target fluence map by combining a plurality of fluence maps corresponding to the plurality of radiation tasks.

According to some embodiments of the present disclosure, the fluence map corresponding to the radiation task may be determined based on the shape change. The shape change may indicate a difference between the fluence map corresponding to the radiation task and a fluence map corresponding to the preceding radiation task. When the difference is relatively small (i.e., the shape change being below the shape change threshold), the fluence map corresponding to the radiation task may be directly used, which can improve the speed of determining the fluence map corresponding to the radiation task. When the difference is relatively large (i.e., the shape change exceeding the shape change threshold), the fluence map corresponding to the radiation task may be updated based on a movement change of the radiation field corresponding to the radiation task during an execution process of the radiation task. The movement change may correlate to the complexity of determining the fluence map corresponding to the radiation task. When the complexity is relatively high (i.e., the movement change exceeding the movement change threshold), the fluence map corresponding to the radiation task may be determined by dividing the radiation task into a plurality of radiation sub-tasks, which can reduce the complexity of determining the fluence map corresponding to the radiation task, improve the speed of determining the fluence map corresponding to the radiation task and the accuracy of the determined fluence map, and further improve the accuracy of a target fluence map so determined, thereby providing an accurate guidance for subsequent treatments and/or preventing treatment accidents.

Figure 1:
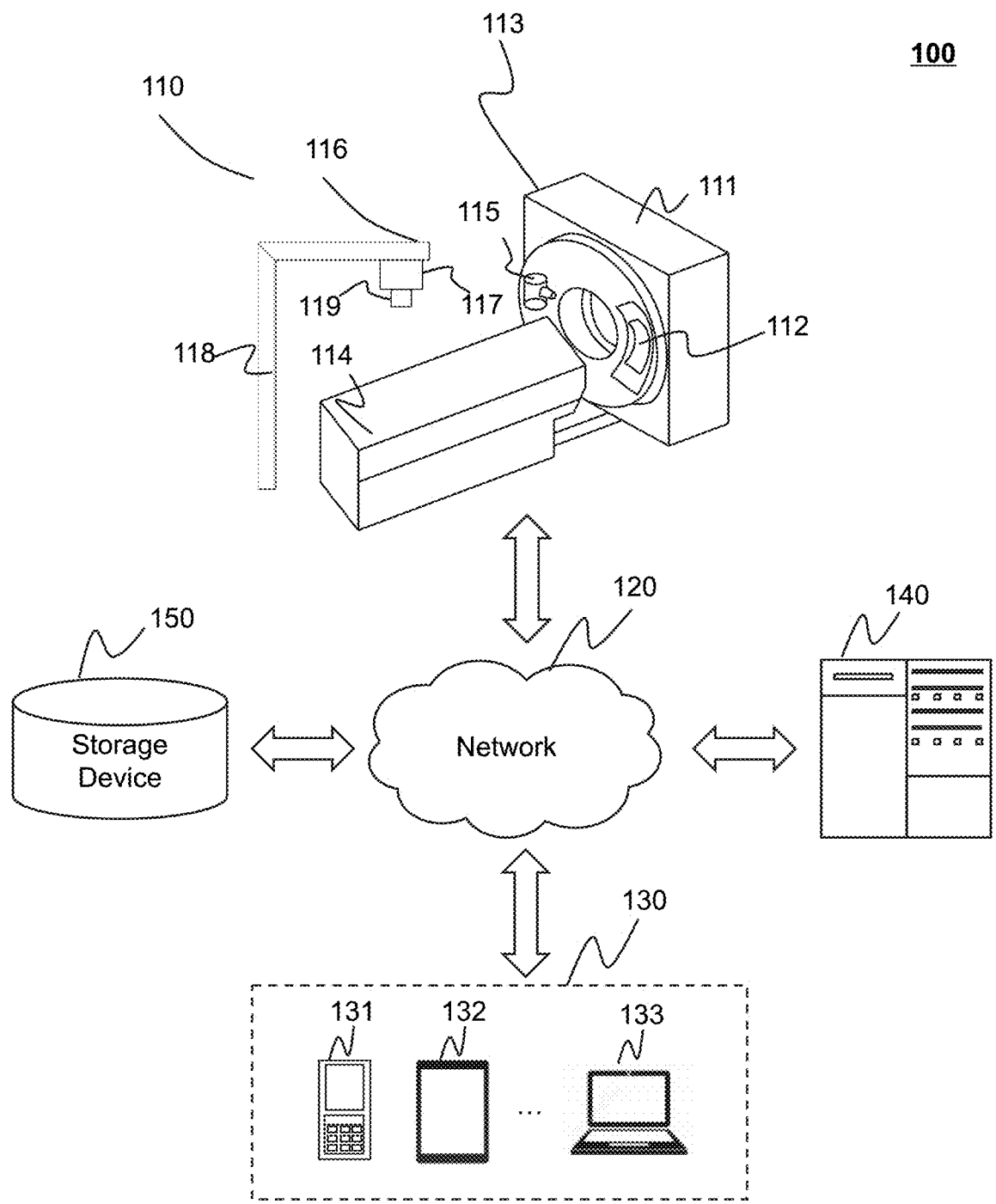
FIG. 1 is a schematic diagram illustrating an exemplary RT system according to some embodiments of the present disclosure.

FIG. 1 is a schematic diagram illustrating an exemplary RT system 100 according to some embodiments of the present disclosure. The RT system 100 may include an RT device 110, a network 120, a terminal 130, a processing device 140, and a storage device 150. In some embodiments, two or more components of the RT system 100 may be connected to and/or communicate with each other via a wireless connection (e.g., the network 120), a wired connection, or a combination thereof. The connection between the components of the RT system 100 may be variable. Merely by way of example, the RT device 110 may be connected to the processing device 140 through the network 120 or directly. As a further example, the storage device 150 may be connected to the processing device 140 through the network 120 or directly.

The RT device 110 may be configured to deliver a radiotherapy treatment to an object. For example, the RT device 110 may deliver one or more radiation beams to a treatment region (also referred to as a target region) (e.g., a tumor region) of an object for causing an alleviation of the object's symptom. A radiation beam may include a plurality of radiation beamlets. In the present disclosure, "subject" and "object" are used interchangeably. The object may include any biological object (e.g., a human being, an animal, a plant, or a portion thereof) and/or a non-biological object (e.g., a phantom). For example, the object may include a specific portion of a body, such as the head, the thorax, the abdomen, or the like, or a combination thereof, of the object. In some embodiments, the RT device 110 may be a conformal radiation therapy device, an image-guided radiation therapy (IGRT) device, a volumetric modulated arc therapy (VMAT) device, an intensity-modulated radiation therapy (IMRT) device, an intensity-modulated arc therapy (IMAT) device, an emission guided radiation therapy (EGRT), or the like. For example, when the RT device 110 is a VMAT device, a gantry in the VMAT device may rotate continuously. As a result, a dose rate of the VMAT device and a position of a multi-leaf collimator (MLC) in the VMAT device may be continuously and rapidly changed, which allows a treatment region of an object to obtain a specified radiation dose while keeping a radiation dose of surrounding tissue of the treatment region within a safe range.

In some embodiments, the RT device 110 may be an IGRT device configured to acquire image data relating to the object and perform a radiotherapy treatment on the object. For example, as illustrated in FIG. 1, the RT device 110 may include an imaging component 113, a treatment component 116, a table 114, or the like. The imaging component 113 may be configured to acquire an image of an object prior to radiotherapy treatment, during the radiotherapy treatment, and/or after the radiotherapy treatment. In some embodiments, the imaging component 113 may include an electronic portal imaging device (EPID), a computed tomography (CT) device, an ultrasound imaging device, a fluoroscopy imaging device, a magnetic resonance imaging (MRI) device, a single photon emission computed tomography (SPECT) device, a positron emission tomography (PET) device, an X-ray imaging device, or the like, or any combination thereof.

In some embodiments, the imaging component 113 may include an imaging radiation source 115, a detector 112, a gantry 111, or the like. The imaging radiation source 115 and the detector 112 may be mounted on the gantry 111. The imaging radiation source 115 may emit radioactive rays to the object. The detector 112 may detect radiation events (e.g., x-ray photons, gamma-ray photons) emitted from the imaging region of the imaging component 113. In some embodiments, the detector 112 may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

The treatment component 116 may be configured to deliver radiotherapy treatment to the object. The treatment component 116 may include a treatment radiation source 117, a gantry 118, and a collimator 119. The treatment radiation source 117 may be configured to emit treatment radiations towards the object. In some embodiments, the treatment radiation source 117 may include a linear accelerator (LINAC). The collimator 119 may be configured to control the shape of the treatment radiations generated by the treatment radiation source 117. In some embodiments, the collimator 119 may include a primary collimator and a secondary collimator. The secondary collimator may include a multi-leaf collimator (MLC) and/or a jaw collimator. The MLC may include a plurality of leaves. The jaw collimator may include a plurality of jaw blades. In some embodiments, a radiation field (also referred to as a radiation region) may be formed by the plurality of leaves and/or jaw blades. In some embodiments, the plurality of leaves and/or jaw blades may be driven by one or more driving components (e.g., a motor) to move to a specific position to form or change the radiation field.

In some embodiments, the imaging component 113 may be spaced by a distance from the treatment component 116. In some embodiments, the gantry 111 of the imaging component 113 and the gantry 118 of the treatment component 116 may share an axis of rotation. The object may be positioned in different positions on the table 114 for imaging and treatment. In some embodiments, the imaging radiation source 115 and the treatment radiation source 117 may be integrated as one radiation source to image and/or treat the object. In some embodiments, the imaging component 113 and the treatment component 116 may share a same gantry. For example, the treatment radiation source 117 may be mounted on the gantry 111 of the imaging component 113. An object may be placed on the table 114 for treatment and/or imaging.

The network 120 may include any suitable network that can facilitate the exchange of information and/or data for the RT system 100. In some embodiments, one or more components of the RT system 100 (e.g., the RT device 110, the terminal 130, the processing device 140, the storage device 150, etc.) may communicate information and/or data with one or more other components of the RT system 100 via the network 120. For example, the processing device 140 may obtain image data from the RT device 110 via the network 120. As another example, the processing device 140 may obtain user instructions from the terminal 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT system 100 may be connected to the network 120 to exchange data and/or information.

Figure 3:
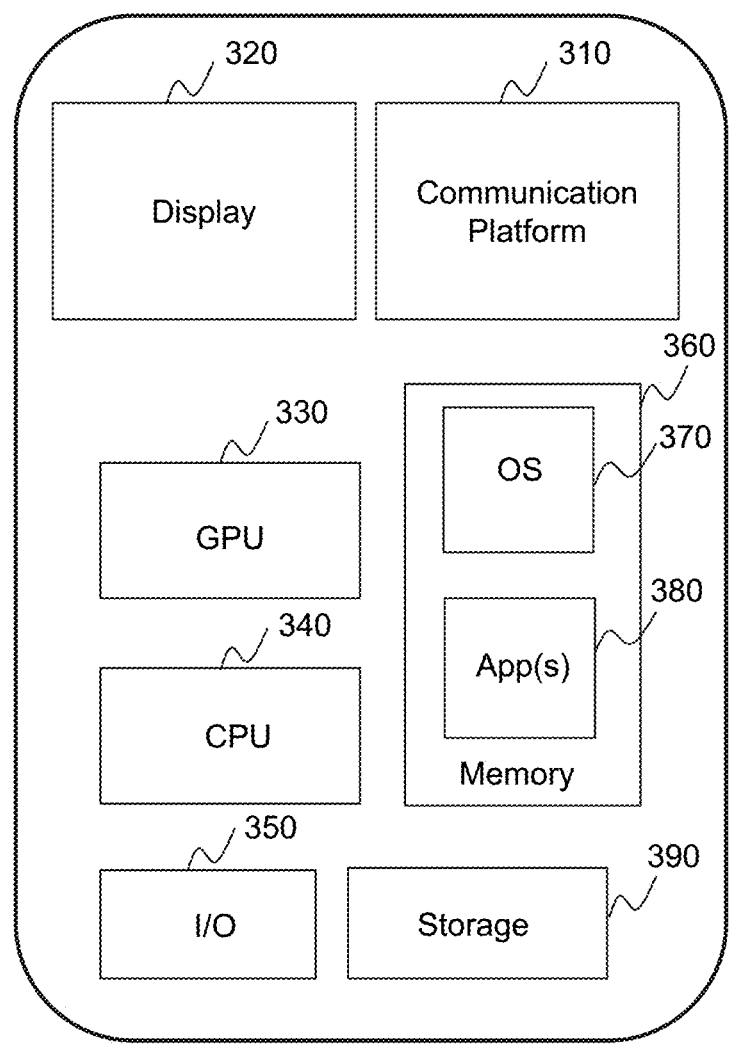
FIG. 3 is a schematic diagram illustrating hardware and/or software components of an exemplary mobile device according to some embodiments of the present disclosure.

The terminal 130 may enable user interaction between a user and the RT system 100. In some embodiments, the terminal 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal 130 may be part of the processing device 140.

The processing device 140 may process information obtained from the RT device 110, the terminal 130, and/or the storage device 150. For example, the processing device 140 may obtain a radiotherapy plan. According to the radiotherapy plan, the processing device 140 may obtain a plurality of radiation tasks. For each of the plurality of radiation tasks, the processing device 140 may determine a fluence map based on whether a shape change between a radiation field corresponding to the radiation task and a radiation field corresponding to a preceding radiation task exceeds a shape change threshold. In some embodiments, the processing device 140 may be a single server or a server group. The server group may be centralized or distributed. In some embodiments, the processing device 140 may be local or remote. For example, the processing device 140 may access information stored in the RT device 110, the terminal 130, and/or the storage device 150 via the network 120. As another example, the processing device 140 may be directly connected to the RT device 110, the terminal 130, and/or the storage device 150 to access stored information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the RT device 110, the terminal 130, and/or the processing device 140. For example, the storage device 150 may store the radiotherapy plan, the plurality of radiation tasks, radiation fields corresponding to the plurality of radiation tasks, and/or the shape change threshold. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components (e.g., the RT device 110, the processing device 140, the terminal 130) of the RT system 100. One or more components of the RT system 100 may access the data and/or instructions stored in the storage device 150 via the network 120. In some embodiments, the storage device 150 may be directly connected to or communicate with one or more other components (e.g., the RT device 110, the processing device 140, the terminal 130) of the RT system 100. In some embodiments, the storage device 150 may be part of the processing device 140.

It should be noted that the above description regarding the RT system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the RT system 100 may include one or more additional components and/or one or more components of the RT system 100 described above may be omitted. For example, the imaging component 113 in the RT device 110 may be omitted. In some embodiments, a component of the RT system 100 may be implemented on two or more sub-components. Two or more components of the RT system 100 may be integrated into a single component. For example, the imaging component 113 in the RT device 110 may be integrated into the treatment component 116.

In some embodiments, processes for fluence map reconstruction disclosed herein may be implemented on a treatment system (e.g., a VMAT system), which may include a treatment device (e.g., a same or similar device as the treatment component 116), the network 120, the storage device 150, the processing device 140, the terminal 130, or the like, or any combination thereof. For illustration purposes, the implementation of the fluence map reconstruction methods on the RT system 100 is described hereinafter, and this is not intended to be limiting.

FIG. 2 is a schematic diagram illustrating exemplary hardware and/or software components of a computing device 200 according to some embodiments of the present disclosure. The computing device 200 may be used to implement any component of the RT system 100 as described herein. For example, the processing device 140 and/or the terminal 130 may be implemented on the computing device 200, respectively, via its hardware, software program, firmware, or a combination thereof. Although only one such computing device is shown, for convenience, the computer functions relating to the RT system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the RT device 110, the terminal 130, the storage device 150, and/or any other component of the RT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data obtained from one or more components of the RT system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program for the processing device 140 to execute to reconstruct a fluence map.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the RT device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 according to some embodiments of the present disclosure. In some embodiments, a terminal 130 and/or a processing device 140 may be implemented on a mobile device 300, respectively. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the RT system 100. User interactions with the information stream may be achieved via the I/O 350 and provided to the processing device 140 and/or other components of the RT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
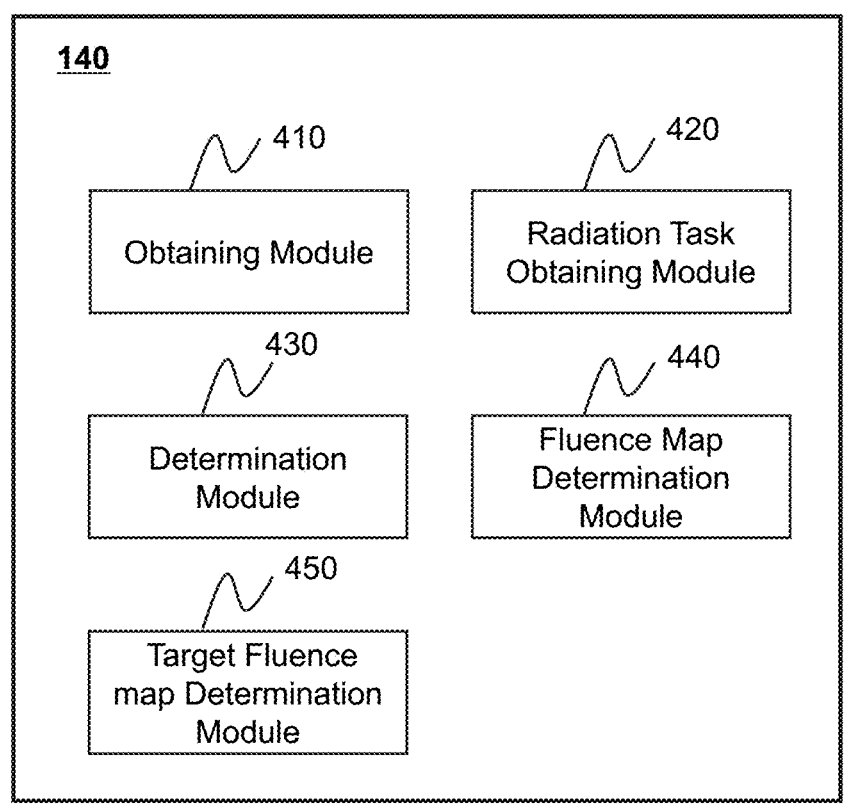
FIG. 4 is a block diagram illustrating an exemplary processing device according to some embodiments of the present disclosure.

FIG. 4 is a block diagram illustrating an exemplary processing device 140 according to some embodiments of the present disclosure. As shown in FIG. 4, the processing device 140 may include an obtaining module 410, a radiation task obtaining module 420, a determination module 430, a fluence map determination module 440, and a target fluence map determination module 450.

The obtaining module 410 may be configured to obtain a radiotherapy plan. More descriptions regarding the obtaining of the radiotherapy plan may be found elsewhere in the present disclosure. See, e.g., operation 510 in FIG. 5 and the description thereof.

The radiation task obtaining module 420 may be configured to obtain a plurality of radiation tasks based on the radiotherapy plan. Each of the plurality of radiation tasks may include a radiation field corresponding to the radiation task. More descriptions regarding the obtaining of the plurality of radiation tasks may be found elsewhere in the present disclosure. See, e.g., operation 520 in FIG. 5 and the description thereof.

The determination module 430 may be configured to determine, for each of the plurality of radiation tasks, whether a shape change between a radiation field corresponding to the radiation task and a radiation field corresponding to a preceding radiation task exceeds a shape change threshold. More descriptions regarding the determining of whether the shape change exceeds the shape change threshold may be found elsewhere in the present disclosure. See, e.g., operation 530 in FIG. 5 and the description thereof.

The fluence map determination module 440 may be configured to determine a fluence map corresponding to the radiation task based on a first determination result of whether the shape change between the radiation field corresponding to the radiation task and the radiation field corresponding to the preceding radiation task exceeds the shape change threshold. In some embodiments, the first determination result may include that the shape change exceeds the shape change threshold and the shape change is less than the shape change threshold. When the shape change exceeds the shape change threshold, the fluence map determination module 440 may update the fluence map corresponding to the radiation task. When the shape change is less than the shape change threshold, the fluence map determination module 440 may designate a fluence map corresponding to the preceding radiation task as the fluence map corresponding to the radiation task. More descriptions regarding the determining of the fluence map corresponding to the radiation task based on the first determination result may be found elsewhere in the present disclosure. See, e.g., FIG. 6 and relevant descriptions thereof.

The target fluence map determination module 450 may be configured to determine a target fluence map by combining a plurality of fluence maps corresponding to the plurality of radiation tasks. More descriptions regarding the determining of the target fluence map may be found elsewhere in the present disclosure. See, e.g., operation 550 in FIG. 5 and relevant descriptions thereof.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules and/or one or more modules described above may be omitted. For example, the processing device 140 may also include a transmission module configured to transmit signals (e.g., electrical signals, electromagnetic signals) to one or more components (e.g., the RT device 110, the terminal 130, the storage device 150) of the RT system 100. As a further example, the processing device 140 may include a storage module (not shown) used to store information and/or data (e.g., the radiotherapy plan, the plurality of radiation tasks, radiation fields corresponding to the plurality of radiation tasks, and/or the shape change threshold) associated with the fluence map reconstruction. Additionally or alternatively, two or more modules may be integrated into a single module and/or a module may be divided into two or more units. For example, the obtaining module 410 and the radiation task obtaining module 420 may be combined as a single module which may both obtain the radiotherapy plan and the plurality of radiation tasks. However, those variations and modifications also fall within the scope of the present disclosure.

Figure 5:
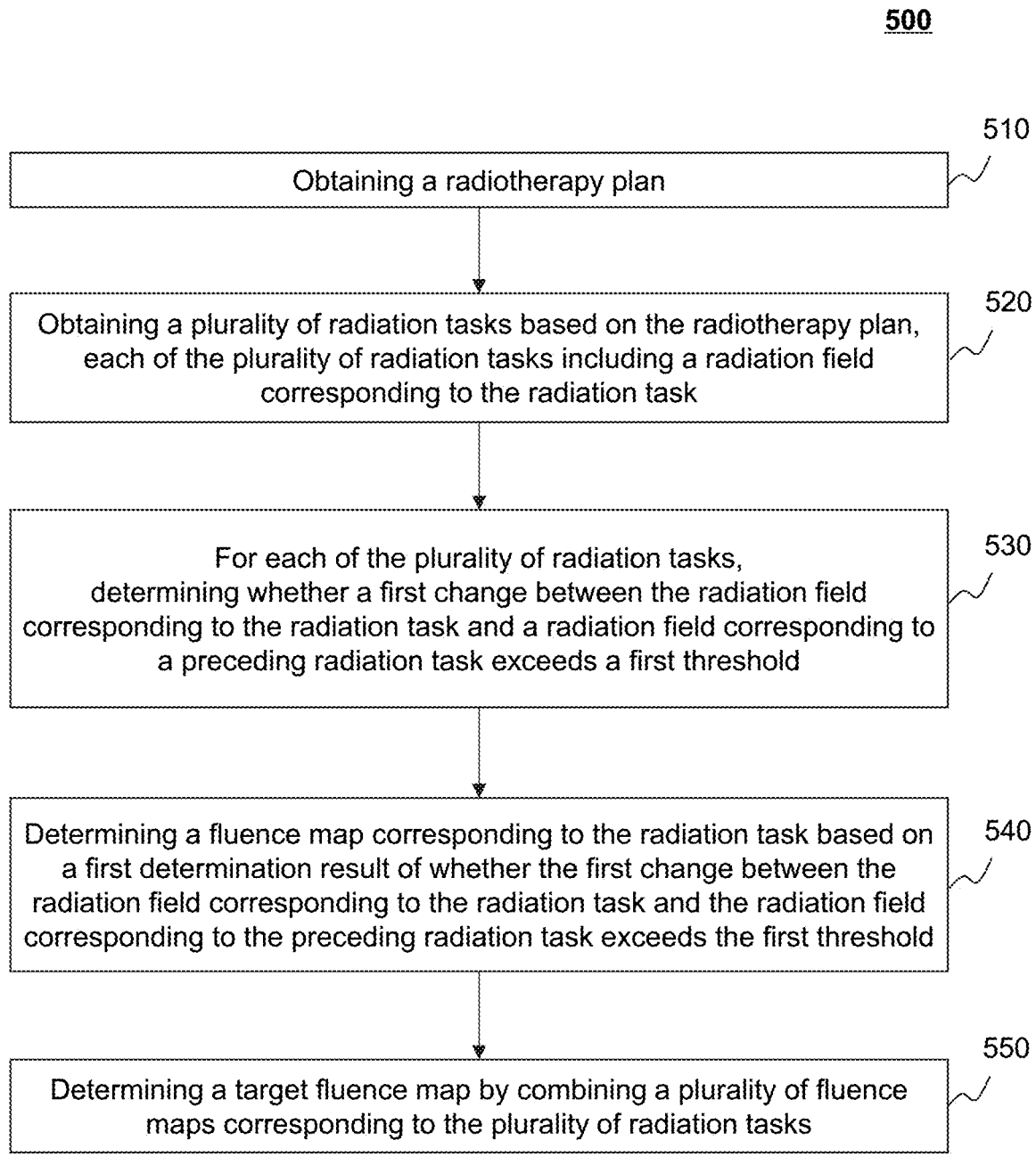
FIG. 5 is a flowchart illustrating an exemplary process for reconstructing a fluence map according to some embodiments of the present disclosure.

FIG. 5 is a flowchart illustrating an exemplary process 500 for reconstructing a fluence map according to some embodiments of the present disclosure. In some embodiments, process 500 may be executed by the RT system 100. For example, the process 500 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 500.

In 510, the processing device 140 (e.g., the obtaining module 410) (e.g., an interface circuit of the processor 210) may obtain a radiotherapy plan.

The radiotherapy plan may describe how a radiotherapy treatment is to be performed on an object (e.g., a patient). For example, the radiotherapy plan may be used to determine how to deliver a radiation beam to allow a target region to receive a prescribed radiation dose while protect a surrounding normal tissue from radiation. The radiotherapy plan may include radiotherapy plan information. The radiotherapy plan information may include but not limited to information related to the target region to be irradiated on the object, radiation doses corresponding to the target region, how one or more radiation beams are delivered to the target region, or the like. The information related to the target region may include, for example, a shape, a size, a location of a target region, an anatomical structure relationship between normal tissue and the target region, etc. The radiation doses corresponding to the target region may include, for example, a total dose (e.g., 0.1 Gy, 10 Gy, 50 Gy, 100 Gy, etc.) of the target region, a dose distribution (e.g., radiation doses at different positions of the target region) in the target region, dose-volume histogram (DVH) in the target region, or the like. In some embodiments, an RT device (e.g., the RT device 110) may treat the target region of the object based on the radiotherapy plan. For example, during an execution process of the radiotherapy plan, the RT device (e.g., the treatment radiation source 117) may generate particle beams or radiation beams (e.g., $\alpha$, $\beta$, $\gamma$ rays, X-rays) based on the radiotherapy plan. Further, the particle beams or the radiation beams may be delivered to the target region of the object.

In some embodiments, the radiotherapy plan may be previously determined and stored in a storage device (e.g., the storage device 150, the storage 220, and/or the storage 390). The processing device 140 may obtain the radiotherapy plan from the storage device via a network (e.g., the network 120).

In 520, the processing device 140 (e.g., the radiation task obtaining module 420) (e.g., the processing circuits of the processor 210) may obtain a plurality of radiation tasks based on the radiotherapy plan.

A radiation task may refer to a process in which a radiation beam of a certain intensity passes through a radiation field with a specific shape within a certain period of time to irradiate the target region to achieve a predetermined radiation dose. In some embodiments, during an execution process of the radiotherapy plan, the RT device (e.g., the RT device 110) may perform a plurality of radiation operations or sessions to deliver to the target region and/or the normal tissue the predetermined radiation dose. Each of the plurality of radiation operations or sessions may be referred to as a radiation task. It should be noted that a sum of radiation doses received by the target region in the plurality of radiation operations constitutes the total dose of the target region in the radiotherapy plan.

In some embodiments, the radiotherapy plan information may include a plurality of radiation tasks, and the processing device 140 may directly obtain the plurality of radiation tasks from the radiotherapy plan information. In some embodiments, the processing device 140 may determine the plurality of radiation tasks based on the radiotherapy plan information. For example, the processing device 140 may determine the plurality of radiation tasks based on the shape of the target region and the radiation doses at different positions of the target region. As another example, if a radiation dose in a central region of the target region is twice that of other regions, the processing device 140 may determine 2 radiation tasks. One of the 2 radiation tasks may correspond to the central region of the target region and a radiation dose of the radiation task may be a, and the other of the 2 radiation tasks may correspond to other regions of the target region and a radiation dose of the radiation task may be a/2. In some embodiments, a radiation task may include a radiation dose corresponding to the radiation task.

Radiation doses corresponding to the plurality of radiation tasks may be the same or different. For example, the radiation doses corresponding to the plurality of radiation tasks may be uniformly set as a default value by the RT system 100.

In some embodiments, a count of the plurality of radiation tasks may be set according to default settings of the RT system 100, for example, 2, 7, 8, 9, 10, 11, 12. Additionally or alternatively, the count of the plurality of radiation tasks may be determined based on the radiotherapy plan or a user instruction. For example, for a volume-modulated radiotherapy plan, the count of the plurality of radiation tasks may be set as a large value (e.g., 12). As another example, for a static intensity-modulated radiotherapy (IMRT) plan, the count of the plurality of radiation tasks may be set as a smaller value (e.g., 2).

In some embodiments, each of the plurality of radiation tasks may include a radiation field corresponding to the radiation task. The radiation field may be formed based on a collimator (e.g., the collimator 119). For example, the radiation field may be formed by a plurality of leaves of an MLC at different positions. As another example, the radiation field may be formed by a plurality of jaw blades of a jaw collimator at different positions. In some embodiments, a shape of the radiation field needs to match a shape of the target region of the object.

In some embodiments, each of a plurality of radiation fields corresponding to the plurality of radiation tasks may be referred to as a segment. In some embodiments, a first segment, a second segment, a third segment, etc., may be used to distinguish different segments. In some embodiments, a count of the plurality of radiation fields may be the same as the count of the plurality of radiation tasks. For example, for the static IMRT plan, the count of the plurality of radiation fields may be 2 (a first segment and a second segment). When at least one leave of the MLC moves to a specified position of the first segment and stops, a radiation source (e.g., the treatment radiation source 117) in the RT device (e.g., the RT device 110) may generate and emit a first radiation beam until a first prescribed dose is delivered. Then, at least one leave moves to a specified position of the second segment and stops, the radiation source may emit a second radiation beam until a second prescribed dose is delivered. The first radiation beam may be the same as or different from the second radiation beam. The first prescribed dose may be the same as or different from the second prescribed dose.

In some embodiments, after the plurality of radiation tasks are performed on the object, the processing device 140 may adjust/update the radiotherapy plan by, for example, adjusting/updating the radiotherapy plan information based on, for example, an anatomical structure of the object. Further, the processing device 140 may adjust/update the plurality of radiation tasks based on the adjusted/updated radiotherapy plan.

In 530, for each of the plurality of radiation tasks, the processing device 140 (e.g., the determination module 430) (e.g., the processing circuits of the processor 210) may determine whether a shape change between a radiation field corresponding to the radiation task and a radiation field corresponding to a preceding radiation task exceeds a shape change threshold.

The preceding radiation task may refer to a radiation task that is adjacent to and performed before the radiation task. In some embodiments, a plurality of preceding radiation tasks may be previously obtained and stored in a storage device (e.g., the storage device 150, the storage 220, and/or the storage 390). In some embodiments, each radiation task may be executed in a time period. The execution of a radiation task starts at a beginning time of the time period and ends at an end time of the time period. The beginning time of the execution of a radiation task may be an end time of the execution of a preceding radiation task of the radiation task. Therefore, the preceding radiation task corresponding to the radiation task may be obtained from the storage device according to the beginning time of the execution of the radiation task.

Radiation fields corresponding to different radiation tasks may be the same or different. For example, a shape of the radiation field corresponding to the radiation task may be different from a shape of the radiation field corresponding to the preceding radiation task. When the RT device (e.g., the RT device 110) performs the radiation task, at least one of the plurality of leaves in MLC may move from a position corresponding to the preceding radiation task to a position corresponding to the radiation task so that the radiation field may change from the radiation field corresponding to the preceding radiation task to the radiation field corresponding to the radiation task.

In some embodiments, the shape change may refer to a change between a shape of the radiation field corresponding to the radiation task and a shape of the radiation field corresponding to the preceding radiation task. In some embodiments, the shape change may include an amount of the change between the shape of the radiation field corresponding to the radiation task and the shape of the radiation field corresponding to the preceding radiation task. As used herein, a shape of a radiation field refers to a contour of the radiation field impinging on an object, e.g., on a target region of the object. In some embodiments, the radiation field of a radiation task may remain constant within the execution process of the radiation task. In some embodiments, the radiation field of a radiation task may change within the execution process of the radiation task. In some embodiments, the radiation field corresponding to the radiation task may be a radiation field corresponding to a time point in the execution process of the radiation task. For example, the radiation field corresponding to the radiation task may be a radiation field corresponding to the beginning time, the end time, or an intermediate time of the execution of the radiation task. In some embodiments, the radiation field corresponding to the preceding radiation task may be a radiation field corresponding to a time point in the execution process of the preceding radiation task. For example, the radiation field corresponding to the preceding radiation task may be a radiation field corresponding to the beginning time, the end time, or an intermediate time of the execution of the preceding radiation task.

In some embodiments, the shape change may be determined based on a movement of at least one of the plurality of leaves or jaw blades. For example, when the RT device (e.g., the RT device 110) performs the preceding radiation task of a radiation task, a leave in an MLC of the RT device moves to a position A. Then when the RT device (e.g., the RT device 110) performs the radiation task, the leave moves to a position B. The shape change may be determined based on a movement amplitude of the leave from the position A to the position B. The movement amplitude may refer to a movement value of a leave in an MLC or a jaw blade in a jaw collimator from one position to another position. Since a radiation field is formed by the plurality of leaves or jaw blades and movement amplitudes of the plurality of leaves or jaws may be different, a movement amplitude used to determine the shape change may be a maximum value of the movement amplitudes of the plurality of leaves or jaw blades. Merely by way of example, to determine whether the shape change exceeds the shape change threshold, the processing device 140 may determine whether the maximum value of the movement amplitudes among the leaves of an MLC or among the jaw blades of a jaw collimator exceeds the shape change threshold. In some embodiments, the movement amplitude used to determine the shape change may be an average value of the movement amplitudes of the plurality of leaves or jaw blades. Merely by way of example, to determine whether the shape change exceeds the shape change threshold, the processing device 140 may determine whether the average value of the movement amplitudes exceeds the shape change threshold.

In some embodiments, the shape change threshold may be default settings of the RT system 100. Merely by way of example, the shape change threshold may be on the millimeter scale, for example, the shape change threshold may be 1 mm, 5 mm, 10 mm, etc. In some embodiments, a value range of the shape change threshold may include 3-7 mm. In some embodiments, the value range of the shape change threshold may include 3-5 mm. In some embodiments, the value range of the shape change threshold may include 5-7 mm. The shape change threshold may be any value within its value range. Merely by way of example, the shape change threshold may be 5 mm. In some embodiments, the shape change threshold may be set according to an actual need. For example, the higher the accuracy of the fluence map, the lower the shape change threshold. In some embodiments, the shape change threshold may be adjustable under different situations, for example, according to different radiotherapy plans.

In 540, the processing device 140 (e.g., the fluence map determination module 440) (e.g., the processing circuits of the processor 210) may determine a fluence map corresponding to the radiation task based on a first determination result of whether the shape change between the radiation field corresponding to the radiation task and the radiation field corresponding to the preceding radiation task exceeds the shape change threshold.

A fluence map may be presented in the form of an image that reflects a status of a device when a radiation beam passes through a collimator (e.g., the collimator 119). For example, the fluence map may reflect a position of a collimator, an intensity of the radiation beam passing through the collimator. In some embodiments, pixel values of pixels in the fluence map may be used to estimate dose of radiation having passed through the target region and/or the normal tissue of the object.

In some embodiments, the first determination result may include that the shape change exceeds the shape change threshold and the shape change is less than the shape change threshold. When the shape change exceeds the shape change threshold, the processing device 140 may update the fluence map corresponding to the radiation task. When the shape change is less than the shape change threshold, the processing device 140 may designate a fluence map corresponding to the preceding radiation task as the fluence map corresponding to the radiation task. More descriptions regarding the determining of the fluence map corresponding to the radiation task based on the first determination result may be found elsewhere in the present disclosure. See, e.g., FIG. 6 and relevant descriptions thereof.

In 550, the processing device 140 (e.g., the target fluence map determination module 450) (e.g., the processing circuits of the processor 210) may determine a target fluence map by combining a plurality of fluence maps corresponding to the plurality of radiation tasks.

In some embodiments, the processing device 140 may determine the target fluence map by performing a weighted combination on the plurality of fluence maps corresponding to the plurality of radiation tasks. In some embodiments, for each of the plurality of fluence maps, the processing device 140 may determine a weight of the fluence map based on pixel values of pixels in the fluence map. For example, the larger the pixel values of pixels in the fluence map, the larger the weight of the fluence map. Additionally or alternatively, the processing device 140 may determine the weight of the fluence map based on radiation in the radiation task corresponding to the fluence map. For example, the larger the radiation in a radiation task corresponding to a fluence map, the larger the weight of the fluence map. As another example, when radiation in a radiation task corresponding to a fluence map is 1 MU, a weight of the fluence map corresponding to the fluence map may be 1. When radiation in another radiation task corresponding to another fluence map is 2 MU, a weight of the another fluence map corresponding to the another fluence map may be 2.

In some embodiments, the processing device 140 may combine the plurality of fluence maps by superimposing (e.g., weighted superimposing or direct superimposing) pixel values of pixels in the plurality of fluence maps. As used herein, in a direct superimposition of fluence maps, the weight of all the fluence map is 1, and the pixel values of all the fluence maps contribute equally to the target fluence map. It is understood that this embodiment described herein are not intended to be limiting. In the present disclosure, the processing device 140 may combine the plurality of fluence maps by other manners, for example, an image combination algorithm.

In some embodiments, the processing device 140 may obtain a target dose distribution (also referred to as a cumulative dose distribution) corresponding to the target fluence map from the target fluence map. Additionally or alternatively, the processing device 140 may determine the target dose distribution corresponding to the target fluence map based on the plurality of fluence maps corresponding to the plurality of radiation tasks. For example, for each of the plurality of fluence maps corresponding to the plurality of radiation tasks, the processing device 140 may obtain a dose distribution corresponding to the fluence map. Further, the processing device 140 may determine the target dose distribution corresponding to the target fluence map based on a plurality of dose distributions corresponding to the plurality of fluence maps. For example, the processing device 140 may determine the target dose distribution by cumulating the plurality of dose distributions.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. For example, the process 500 may include an additional transmitting operation to transmit the target fluence map to a terminal device (e.g., a terminal 130 of a doctor) for display. As another example, the process 500 may include an additional storing operation to store information and/or data (e.g., the radiotherapy plan, the plurality of radiation tasks, radiation fields corresponding to the plurality of radiation tasks, and/or the shape change threshold) associated with the fluence map reconstruction in a storage device (e.g., the storage device 150) disclosed elsewhere in the present disclosure. In some embodiments, the first determination result may include that the shape change is equal to the shape change threshold. When the shape change is equal to the shape change threshold, the processing device 140 may perform any operation of designating a fluence map corresponding to the preceding radiation task as the fluence map corresponding to the radiation task or updating the fluence map corresponding to the radiation task.

Figure 6:
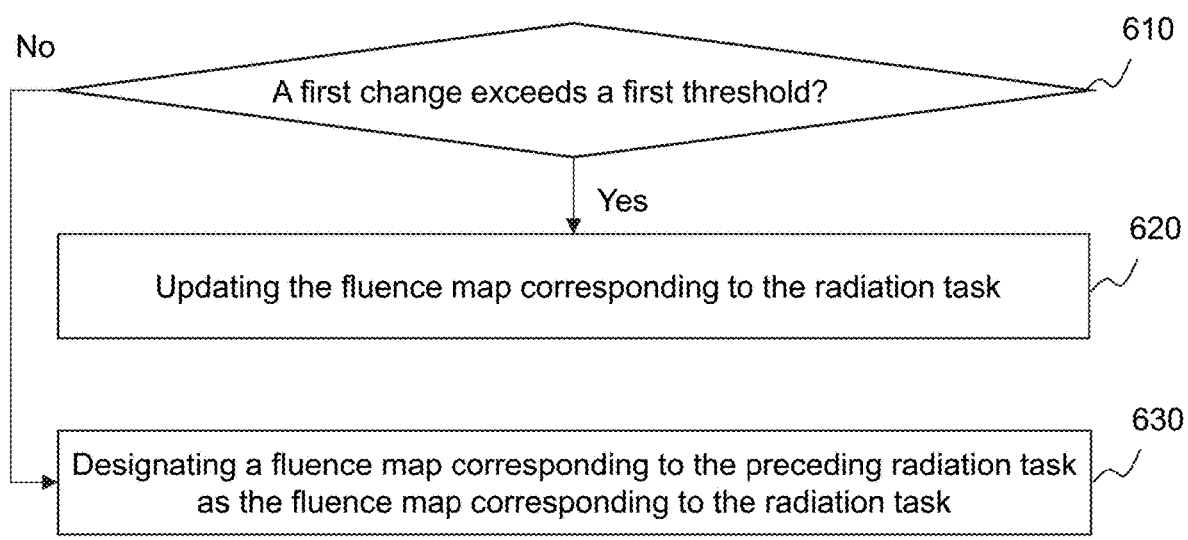
FIG. 6 is a flowchart illustrating an exemplary process for determining a fluence map corresponding to a radiation task based on a first determination result according to some embodiments of the present disclosure.

FIG. 6 is a flowchart illustrating an exemplary process 600 for determining a fluence map corresponding to a radiation task based on a first determination result according to some embodiments of the present disclosure. In some embodiments, process 600 may be executed by the RT system 100. For example, the process 600 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 600.

In 610, the processing device 140 (e.g., the determination module 430) (e.g., the processing circuits of the processor 210) may determine whether a shape change between a radiation field corresponding to a radiation task and a radiation field corresponding to a preceding radiation task exceeds a shape change threshold. Operation 610 may be performed in a similar manner as operation 530 as described in connection with FIG. 5, and the descriptions thereof are not repeated here.

The shape change may indicate a difference between the fluence map corresponding to the radiation task and a fluence map corresponding to the preceding radiation task. When the shape change is less than the shape change threshold (i.e., the difference is relatively small), the processing device 140 may directly designate a fluence map corresponding to the preceding radiation task as the fluence map corresponding to the radiation task, which can improve the speed of determining the fluence map corresponding to the radiation task. When the shape change exceeds the shape change threshold (i.e., the difference is relatively large), the processing device 140 may perform operation 620.

In 620, the processing device 140 (e.g., the fluence map determination module 440) (e.g., the processing circuits of the processor 210) may update a fluence map corresponding to the radiation task.

The processing device 140 may determine the fluence map corresponding to the radiation task based on an EPID image corresponding to the radiation task. The EPID image corresponding to the radiation task may be obtained by an auxiliary device (e.g., an EPID) of an RT device (e.g., the RT device 110) during a process of the RT device performing the radiation task. For example, during the execution process of the radiation task, the EPID may detect rays passing through the object and convert the detected rays into electrical or digital signals (e.g., projection data). Further, the processing device 140 may obtain the electrical or digital signals and generate the EPID image corresponding to the radiation task based on the electrical or digital signals. In some embodiments, the auxiliary device may be an external device operably connected to the RT device via the network 120. Additionally or alternatively, the auxiliary device may be integrated in the RT device.

In some embodiments, a radiation task may correspond to one or more EPID images. The processing device 140 may obtain one or more EPID images during the execution process of the radiation task. For example, the processing device 140 may generate an EPID image using all projection data obtained during the execution process of the radiation task. As another example, the processing device 140 may divide the execution process of the radiation task into a plurality of consecutive time periods. For each of the plurality of consecutive time periods, the processing device 140 may generate an EPID image based on projection data obtained in the time period.

The processing device 140 may obtain an EPID image corresponding to the radiation task from the EPID. For example, the processing device 140 may obtain any EPID image form one or more EPID images corresponding to the radiation task. Further, the processing device 140 may determine the fluence map corresponding to the radiation task by converting the EPID image corresponding to the radiation task. For example, the processing device 140 may convert the EPID image corresponding to the radiation task by performing operations of a pre-processing, a de-scattering, an image back-projection, and a digital image processing, etc. These operations may be used to improve the accuracy of the fluence map. The pre-processing may refer to an image processing performed on an image before further processing the image. The pre-processing may include a denoising processing, a grayscale transformation, a geometric transformation, an image enhancement, or the like, or any combination thereof. The image back-projection may include but is not limited to a deconvolution. The deconvolution may include but is not limited to a Wiener filter deconvolution, an iterative deconvolution, or the like, or any combination thereof.

The de-scattering may refer to an operation used to remove, correct, or reduce the interference of scattered rays on the image. For instance, the de-scattering may be performed by a Monte Carlo simulation. In a Monte Carlo simulation for de-scattering, scattered particles in the radiation beam and a penetration rate of the scattered particles may be marked by a position and a direction of each of the scattered particles. According to the marked scattered particles and the penetration rate, a scatter ratio corresponding to the radiation task and a penetration rate of the object may be obtained. The image may be processed based on the scatter ratio and the penetration rate.

Digital image processing may refer to one or more operations used to process an image using a computer (e.g., the processing device 200). For example, the computer may perform a recognition operation and/or a calculation operation on an image (e.g., the EPID image corresponding to the radiation task). Further, the computer may mark the image based on the recognition result and/or the calculation result, which may display the desired information on the marked image. For example, the computer may mark the image as an illuminated region (i.e., a region where rays directly irradiate the object) and a blocked region (i.e., a region where rays are blocked by a collimator). Merely by way of example, the digital image processing may be an image binarization operation. The image binarization operation may refer to an algorithm used to set a gray value of each pixel in an image to 0 or 1. For example, when a gray value of a pixel in the image is larger than or equal to a preset threshold, the gray value of the pixel may be marked as 1, which may indicate that the pixel is located in the illuminated region. When the gray value of the pixel in the image is less than the preset threshold, the gray value of the pixel may be marked as 0, which may indicate that the pixel is located in the blocked region.

In some embodiments, at least one of the operations of the de-scattering or the image back-projection may be omitted. The processing device 140 may convert the EPID image corresponding to the radiation task by performing the pre-processing and the digital image processing, which may increase the speed of determining the fluence map. Compared with the above embodiment in which the operations of the pre-processing, the de-scattering, the image back-projection, and the digital image processing are performed, the process of determining the fluence map corresponding to the radiation task in this embodiment is relatively simple, thereby a better accuracy of the fluence map may be obtained. For example, if the manner of the de-scattering is the Monte Carlo manner, the scattered particles in the radiation beam and the penetration rate of the scattered particles need to be marked and calculated. The process of determining the fluence map corresponding to the radiation task as described in the embodiments may avoid the complicated calculation of the scattered particles and the penetration rate, thereby reducing the amount of calculation and improving the calculation speed. More descriptions regarding the determining of the fluence map corresponding to the radiation task based on the EPID image may be found elsewhere in the present disclosure. See, e.g., FIG. 8 and relevant descriptions thereof.

In some embodiments, when the shape change exceeds the shape change threshold, the processing device 140 may determine the fluence map corresponding to the radiation task based on a movement change of the radiation field corresponding to the radiation task during the execution process of the radiation task exceeds a movement change threshold. For example, the processing device 140 may determine whether the movement change exceeds a movement change threshold. Further, the processing device 140 may determine the fluence map corresponding to the radiation task based on a second determination result of whether the movement change of the radiation field corresponding to the radiation task exceeds the movement change threshold. The second determination result may include that the movement change exceeds the movement change threshold. When the movement change exceeds the movement change threshold, the processing device 140 may determine a plurality of radiation sub-tasks based on the movement change threshold. Further, the processing device 140 may determine the fluence map corresponding to the radiation task based on the plurality of radiation sub-tasks. More descriptions regarding the determining of the fluence map based on the second determination result may be found elsewhere in the present disclosure. See, e.g., FIG. 7 and relevant descriptions thereof.

In some embodiments, when the radiation task is performed in the case of a single gantry angle or a small gantry angle span, movement amplitudes of the plurality of leaves may be relatively large (the shape change exceeds the shape change threshold), which may improve the complexity of determining the fluence map corresponding to the radiation task. In this case, according to some embodiments of the present application, the processing device 140 may divide the radiation task into the plurality of radiation sub-tasks and determine the fluence map corresponding to the radiation task based on the plurality of radiation sub-tasks, which may reduce the complexity of determining the fluence map corresponding to the radiation task. In some embodiments, when the radiation task is performed in the case of a plurality of gantry angles, the movement amplitudes of the plurality of leaves and a change between the fluence map corresponding to the radiation task and the fluence map corresponding to the preceding radiation task may be relatively small (the shape change may be less than or equal to the shape change threshold). In this case, operation 630 may be performed.

In 630, the processing device 140 (e.g., the fluence map determination module 440) (e.g., the processing circuits of the processor 210) may designate a fluence map corresponding to the preceding radiation task as the fluence map corresponding to the radiation task.

In some embodiments, the fluence map corresponding to the preceding radiation task may be previously obtained and stored in a storage device (e.g., the storage device 150, the storage 220, and/or the storage 390). The processing device 140 may obtain the fluence map corresponding to the preceding radiation task from the storage device.

According to some embodiments of the present application, the fluence map corresponding to the preceding radiation task is designated as the fluence map corresponding to the radiation task, which may avoid the operations of determining the fluence map corresponding to the radiation task, thereby reducing the amount of calculation and improving the speed of determining the fluence map corresponding to the radiation task.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above. In some embodiments, the processing device 140 may determine a fluence map at any time point (e.g., the beginning time, the end time, or the intermediate time) in the execution process of the radiation task as the fluence map corresponding to the radiation task.

Figure 7:
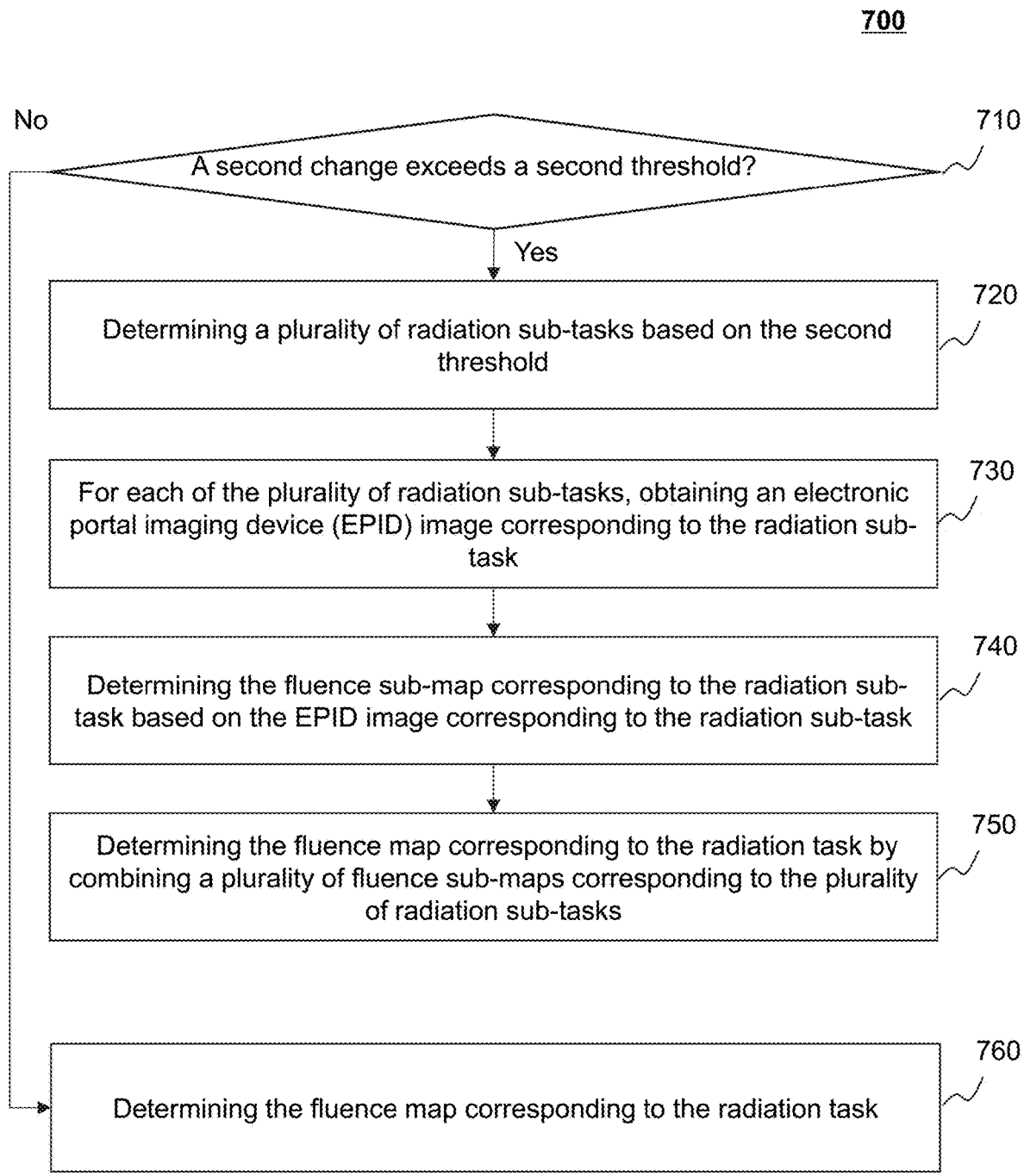
FIG. 7 is a flowchart illustrating an exemplary process for determining a fluence map corresponding to a radiation task based on a second determination result according to some embodiments of the present disclosure.

FIG. 7 is a flowchart illustrating an exemplary process 700 for determining a fluence map corresponding to a radiation task based on a second determination result according to some embodiments of the present disclosure. In some embodiments, process 700 may be executed by the RT system 100. For example, the process 700 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 700.

As described in connection with operation 620, when the shape change exceeds the shape change threshold, the processing device 140 may update the fluence map corresponding to the radiation task based on the movement change.

In 710, the processing device 140 (e.g., the fluence map determination module 440) (e.g., the processing circuits of the processor 210) may determine whether a movement change of the radiation field corresponding to the radiation task during an execution process of the radiation task exceeds a movement change threshold.

As described in connection with operation 530, each radiation task is executed in a time period. The execution of the radiation task starts at a beginning time of the time period and ends at an end time of the time period. The movement change may refer to a change between a radiation field corresponding to the beginning time of the time period and a radiation field corresponding to the end time of the time period. In some embodiments, a value of the movement change may be larger than 0.

The movement change may be determined based on a movement amplitude of at least one of the plurality of leaves or jaws during the execution process of the radiation task. Since a radiation field may be formed by the plurality of leaves or jaw blades and movement amplitudes of the plurality of leaves or jaw blades may be different, a movement amplitude used to determine the movement change may be a maximum value of the movement amplitudes of the plurality of leaves or jaw blades. Merely by way of example, to determine whether the movement change exceeds the movement change threshold, the processing device 140 may determine whether the maximum value of the movement amplitudes exceeds the movement change threshold. In some embodiments, the movement amplitude used to determine the movement change may be an average value of the movement amplitudes of the plurality of leaves or jaw blades. Merely by way of example, to determine whether the movement change exceeds the movement change threshold, the processing device 140 may determine whether the average value of the movement amplitudes exceeds the movement change threshold.

In some embodiments, the movement change threshold may be set according to default settings of the RT system 100. Merely by way of example, the movement change threshold may be in the order of a few millimeters. For example, the movement change threshold may be 3 mm, 5 mm, 6 mm, etc. In some embodiments, a value range of the movement change threshold may include 3-7 mm. In certain preferred embodiments, the value range of the movement change threshold may include 3-5 mm. In some embodiments, the value range of the movement change threshold may include 5-7 mm. The movement change threshold may be any value within its value range. Preferably, the movement change threshold may be 5 mm. In some embodiments, the movement change threshold may be set according to an actual need. In some embodiments, the movement change threshold may be set based on the shape change threshold. Merely by way of example, the movement change threshold may be the same as the shape change threshold. For example, the movement change threshold and the shape change threshold may be both 5 mm. Merely by way of another example, the movement change threshold may be less than the shape change threshold. For example, the shape change threshold is 6 mm and the movement change threshold is 5 mm.

In some embodiments, the processing device 140 may determine the fluence map corresponding to the radiation task based on a second determination result of whether the movement change of the radiation field corresponding to the radiation task exceeds the movement change threshold. The second determination result may include that the movement change exceeds the movement change threshold and the movement change is less than or equal to the movement change threshold. When the movement change exceeds the movement change threshold, the processing device 140 may perform operation 720. When the movement change is less than or equal to the movement change threshold, the processing device 140 may perform operation 760.

In 720, the processing device 140 (e.g., the fluence map determination module 440) (e.g., the processing circuits of the processor 210) may determine a plurality of radiation sub-tasks based on the movement change threshold.

When the movement change exceeds the movement change threshold, the processing device 140 may divide the radiation task into the plurality of radiation sub-tasks (e.g., 2, 3, 8, etc.). Further, the processing device 140 may divide the radiation field corresponding to the radiation task into a plurality of radiation sub-fields (also referred to as sub-segments) corresponding to the plurality of radiation sub-tasks. In some embodiments, a change of radiation sub-fields corresponding to two neighboring radiation sub-tasks may be within the movement change threshold. For example, when the movement change exceeds the movement change threshold, the processing device 140 may divide the radiation task into 2 radiation sub-tasks and a change of radiation sub-fields corresponding to the 2 radiation sub-tasks may be within the movement change threshold. As another example, the processing device 140 may divide the radiation task into 3 radiation sub-tasks (e.g., a radiation sub-task A, a radiation sub-task B, a radiation sub-task C) and a change of radiation sub-fields corresponding to two neighboring radiation sub-tasks (e.g., the radiation sub-task A and the radiation sub-task B, the radiation sub-task B and the radiation sub-task C) may be within the movement change threshold. In some embodiments, for each of the plurality of radiation sub-tasks, a change of a radiation sub-field corresponding to the radiation sub-task during an execution process of the radiation sub-task is within the movement change threshold. For example, when the radiation task is divided into the radiation sub-task A, the radiation sub-task B, and the radiation sub-task C, for each of the radiation sub-task A, the radiation sub-task B, and the radiation sub-task C, a change of a radiation sub-field corresponding to the radiation sub-task during an execution process of the radiation sub-task is within the movement change threshold. In some embodiments, for each of the plurality of radiation sub-fields, positions of leaves or jaw blades used to form the radiation sub-field may be unchanged or almost unchanged. In such cases, the radiation sub-field do not need to be further divided, nor does the radiation sub-task corresponding to the radiation sub-field.

Further, the processing device 140 may determine the fluence map corresponding to the radiation task based on the plurality of radiation sub-tasks. In some embodiments, for each of the plurality of radiation sub-tasks, the processing device 140 may determine a fluence sub-map corresponding to the radiation sub-task. For example, the processing device 140 may obtain an EPID image corresponding to the radiation sub-task. According to the EPID image corresponding to the radiation sub-task, the processing device 140 may determine the fluence sub-map corresponding to the radiation sub-task. Further, the processing device 140 may determine the fluence map corresponding to the radiation task by combining a plurality of fluence sub-maps corresponding to the plurality of radiation sub-tasks. More descriptions regarding the determining of the fluence map corresponding to the radiation task based on the plurality of radiation sub-tasks may be found elsewhere in the present disclosure. See, e.g., operations 730-750 and relevant descriptions thereof.

When the shape change exceeds the shape change threshold, the fluence map corresponding to the radiation task is a complicated fluence map within multi-state superposition. When the movement change exceeds the movement change threshold, the complicated fluence map is divided into the plurality of radiation sub-tasks. A fluence sub-map corresponding to each of the plurality of radiation sub-tasks is a relatively simple fluence map. The fluence map corresponding to the radiation task may be determined by determining the plurality of fluence sub-maps corresponding to the plurality of radiation sub-tasks, which reduces the complexity of reconstructing the fluence map corresponding to the radiation task, thereby improving the speed and accuracy of reconstructing the fluence map corresponding to the radiation task.

In 730, for each of the plurality of radiation sub-tasks, the processing device 140 (e.g., the fluence map determination module 440) (e.g., the processing circuits of the processor 210) may obtain an EPID image corresponding to the radiation sub-task.

During a process of the radiation sub-task performed by an RT device (e.g., the RT device 110), the EPID image corresponding to the radiation sub-task may be obtained by an auxiliary device (e.g., an EPID) of the RT device. Further, the processing device 140 may obtain the EPID image corresponding to the radiation sub-task from the auxiliary device.

In 740, the processing device 140 (e.g., the fluence map determination module 440) (e.g., the processing circuits of the processor 210) may determine the fluence sub-map corresponding to the radiation sub-task based on the EPID image corresponding to the radiation sub-task.

In some embodiments, the processing device 140 may determine the fluence sub-map corresponding to the radiation sub-task by converting the EPID image corresponding to the sub-radiation task. For example, the processing device 140 may convert the EPID image corresponding to the radiation sub-task by performing operations of a pre-processing, a de-scattering, an image back-projection, and a digital image processing, etc. In some embodiments, at least one of the operations of the de-scattering or the image back-projection may be omitted. The converting of the EPID image corresponding to the sub-radiation task may be performed in a similar manner as that of operation 620 as described in connection with FIG. 6, and the descriptions thereof are not repeated here.

In 750, the processing device 140 (e.g., the fluence map determination module 440) (e.g., the processing circuits of the processor 210) may determine the fluence map corresponding to the radiation task by combining the plurality of fluence sub-maps corresponding to the plurality of radiation sub-tasks.

In some embodiments, the processing device 140 may determine the fluence map corresponding to the radiation task by performing a weighted combination on the plurality of fluence sub-maps corresponding to the plurality of radiation sub-tasks. The determining of the fluence map corresponding to the radiation task by combining the plurality of fluence sub-maps may be performed in a similar manner as that of operation 550 as described in connection with FIG. 5, and the descriptions thereof are not repeated here.

In 760, the processing device 140 (e.g., the fluence map determination module 440) (e.g., the processing circuits of the processor 210) may determine the fluence map corresponding to the radiation task.

When the movement change is less than or equal to the movement change threshold, which means that a change of the radiation field corresponding to the radiation task during the execution process of the radiation task is relatively small or even equal to 0. Since the movement change may be determined based on the maximum value of the movement amplitudes of the plurality of leaves, the movement amplitudes of the plurality of leaves are relatively small or the plurality of leaves are even close to static. In this case, the radiation task does not need to be divided into the plurality of radiation sub-tasks, which may simplify the process of reconstructing the fluence map corresponding to the radiation task and reduce the complexity of the calculation in the process of reconstructing the fluence map corresponding to the radiation task. Merely by way of example, if the manner of the de-scattering is the Monte Carlo manner, compared with the embodiment (also referred to as a division embodiment) in which the radiation task is divided into the plurality of radiation tasks, a count of the scattered particles to be calculated in this embodiment may be reduced. It is assumed that the count of the scattered particles to be calculated in this embodiment may be denoted as A, and a count of the scattered particles to be calculated in the division embodiment may be denoted as B. In some embodiments, A may be reduced to B/50-B/25. In some embodiments, A may be reduced to B/50, B/25, or B/40. For instance, A may be reduced to B/25, which means that the time of calculating the scattered particles in this embodiment may be reduced to about ½₅ of the time of calculating the scattered particles in the division embodiment, thereby reducing the complexity of the calculation in the process of reconstructing the fluence map corresponding to the radiation task.

In some embodiments, the processing device 140 may determine the fluence map corresponding to the radiation task based on an EPID image corresponding to the radiation task. The determining of the fluence map corresponding to the radiation task based on the EPID image corresponding to the radiation task may be performed in a similar manner as that of operation 620 as described in connection with FIG. 6, and the descriptions thereof are not repeated here.

It should be noted that the above description regarding the process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 700 may be accomplished with one or more additional operations not described and/or without one or more of the operations discussed above.

Figure 8:
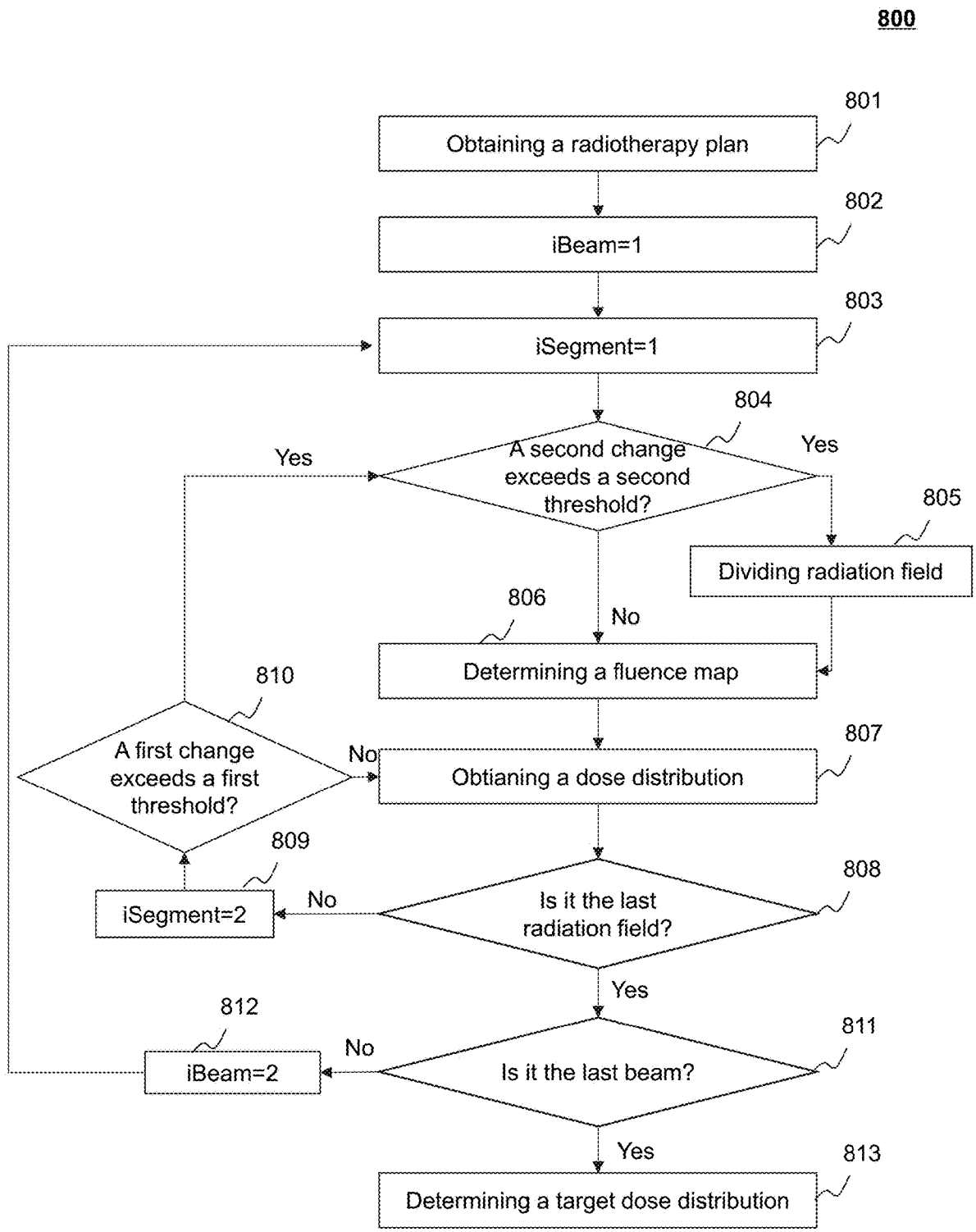
FIG. 8 is a flowchart illustrating an exemplary process for determining a fluence map according to some embodiments of the present disclosure.

FIG. 8 is a flowchart illustrating an exemplary process for determining a fluence map according to some embodiments of the present disclosure. In some embodiments, process 800 may be executed by the RT system 100. For example, the process 800 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 800.

In 801, the processing device 140 (e.g., the obtaining module 410) (e.g., the interface circuits of the processor 210) may obtain a radiotherapy plan. Further, the processing device 140 may obtain a plurality of radiation tasks based on the radiotherapy plan. More descriptions regarding the obtaining of the radiotherapy plan and the plurality of radiation tasks may be found elsewhere in the present disclosure. See, e.g., operations 510 and 520 in FIG. 5 and relevant descriptions thereof.

In 802, the processing device 140 (e.g., the radiation task obtaining module 420) (e.g., the processing circuits of the processor 210) may cause an RT device (e.g., the RT device 110) to generate and emit a radiation beam (e.g., a first radiation beam (denoted as iBeam=1)) based on the radiotherapy plan. In some embodiment, the radiation beam may include one or more segments corresponding to one or more radiation tasks.

In 803, for each (e.g., a first radiation task to be performed among the plurality of radiation tasks) of the plurality of radiation tasks, the processing device 140 (e.g., the radiation task obtaining module 420) (e.g., the processing circuits of the processor 210) may set an MLC in the RT device to form a radiation field (e.g., a first radiation field (denoted as iSegment=1)) corresponding to the radiation task. A radiation field may correspond to a radiation task. The RT device may perform the radiation task by emitting the radiation beam through the radiation field corresponding to the radiation task to irradiate a target region.

In 804, the processing device 140 (e.g., the determination module 430) (e.g., the processing circuits of the processor 210) may determine whether a maximum value (i.e., a movement change) of movement amplitudes of the plurality of leaves in the MLC during an execution process of the radiation task corresponding to the radiation field exceeds a movement change threshold. When the maximum value of the movement amplitudes exceeds the movement change threshold, the processing device 140 may perform operation 805. When the maximum value of the movement amplitudes is less than or equal to the movement change threshold, the processing device 140 may perform operation 806.

In 805, the processing device 140 (e.g., the fluence map determination module 440) (e.g., the processing circuits of the processor 210) may divide the radiation field into a plurality of radiation sub-fields. A radiation sub-field may correspond to a radiation sub-task.

In 806, the processing device 140 (e.g., the fluence map determination module 440) (e.g., the processing circuits of the processor 210) may determine a fluence map corresponding to the radiation field.

In some embodiments, the processing device 140 may determine the fluence map corresponding to the radiation field based on the plurality of radiation sub-fields. The determining of the fluence map corresponding to the radiation field may be performed in a similar manner as described in connection with FIG. 7, and the descriptions thereof are not repeated here.

In some embodiments, the processing device 140 may determine the fluence map corresponding to the radiation field based on an EPID image corresponding to the radiation field. The determining of the fluence map corresponding to the radiation field based on the EPID image may be performed in a similar manner as that of operation 620 as described in connection with FIG. 6, and the descriptions thereof are not repeated here.

In 807, the processing device 140 (e.g., the target fluence map determination module 450) (e.g., the processing circuits of the processor 210) may obtain a dose distribution corresponding to the radiation field from the fluence map corresponding to the radiation field.

In 808, the processing device 140 (e.g., the target fluence map determination module 450) (e.g., the processing circuits of the processor 210) may determine whether the radiation field is a last radiation field (i.e., the radiation task corresponding to the radiation field is a last radiation task among the plurality of radiation tasks). When the radiation field is the last radiation field (i.e., the radiation task corresponding to the radiation field is the last radiation task), the processing device 140 may perform operation 811. When the radiation field is not the last radiation field (i.e., the radiation task corresponding to the radiation field is not the last radiation task), the processing device 140 may perform operation 809.

In 809, the processing device 140 (e.g., the radiation task obtaining module 420) (e.g., the processing circuits of the processor 210) may set the MLC in the RT device to form a next radiation field (e.g., a second radiation field (denoted as iSegment=2)) corresponding to a next radiation task (e.g., a second radiation task to be performed among the plurality of radiation tasks).

In 810, the processing device 140 (e.g., the determination module 430) (e.g., the processing circuits of the processor 210) may determine whether a shape change between the next radiation field and the radiation field exceeds a shape change threshold. When the shape change exceeds the shape change threshold, the processing device 140 may perform operations 804-808 again. When the shape change is less than or equal to the shape change threshold, the processing device 140 may designate the fluence map corresponding to the radiation field as a fluence map corresponding to the next radiation field and perform operations 807-808.

In 811, the processing device 140 (e.g., the target fluence map determination module 450) (e.g., the processing circuits of the processor 210) may determine whether the radiation beam is a last radiation beam. When the radiation beam is the last radiation beam, the processing device 140 may perform operation 813. When the radiation beam is not the last radiation beam, the processing device 140 may perform operation 812.

In 812, the processing device 140 (e.g., the radiation task obtaining module 420) (e.g., the processing circuits of the processor 210) may cause the RT device to generate and emit a next radiation beam (e.g., a second radiation beam (denoted as iBeam=2)) based on radiotherapy plan. Further, the processing device 140 may perform operations 803-811 again.

In 813, the processing device 140 (e.g., the target fluence map determination module 450) (e.g., the processing circuits of the processor 210) may determine a target dose distribution by cumulating all dose distributions obtained in the operation 807, for example, the dose distribution corresponding to the radiation field, a dose distribution corresponding to the next radiation field, etc.

As illustrated FIG. 8, when the radiation field (e.g., the first radiation field) is not the last radiation field, for the next radiation field (e.g., the second radiation field), the processing device 140 may determine whether a fluence map corresponding to the next radiation field needs to be re-determined based on the shape change between the radiation field and next first radiation field. When the shape change is less than or equal to the shape change threshold, the processing device 140 does not need to re-determine the fluence map corresponding to the next radiation field, but directly designates the fluence map corresponding to the radiation field as the fluence map corresponding to the next radiation field, thereby improving the speed of reconstructing the fluence map corresponding to the next radiation field.

It should be noted that the above description regarding the process 800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 800 may be accomplished with one or more additional operations not described and/or without one or more of the operations discussed above.

Figure 9:
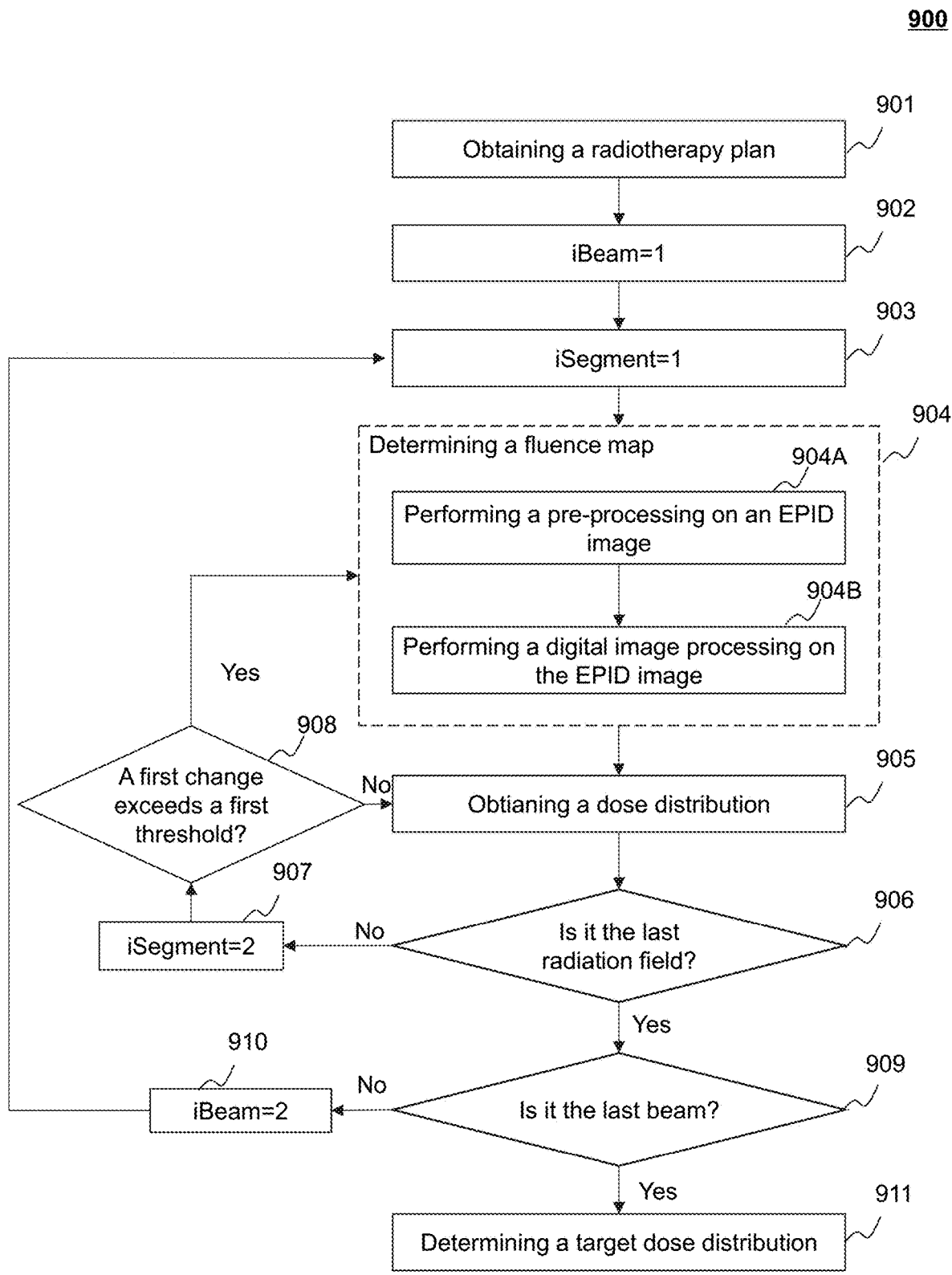
FIG. 9 is a flowchart illustrating an exemplary process for determining a fluence map according to some embodiments of the present disclosure.
Figure 11A:
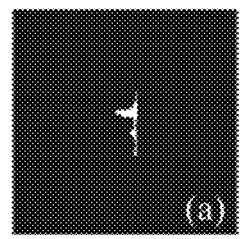
FIGS. 11A-11H are schematic diagrams illustrating 8 fluence images reconstructed based on 8 radiation tasks corresponding to a radiotherapy plan according to some embodiments of the present disclosure.
Figure 11B:
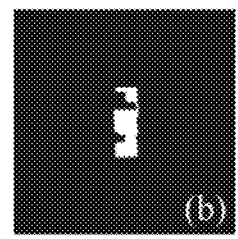
Figure 11C:
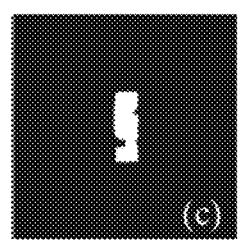
Figure 11D:
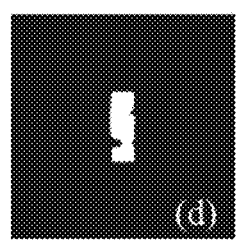
Figure 11E:
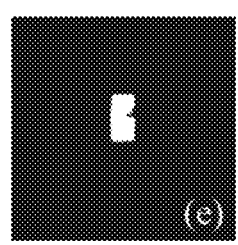
Figure 11F:
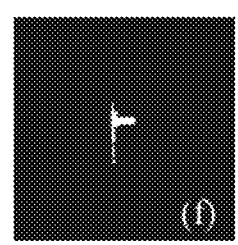
Figure 11G:
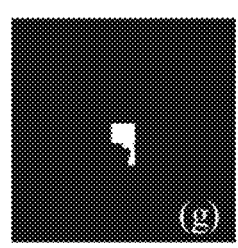
Figure 11H:
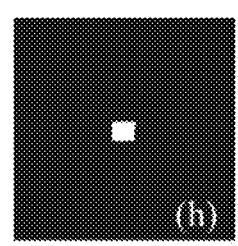

FIG. 9 is a flowchart illustrating an exemplary process for determining a fluence map according to some embodiments of the present disclosure. In some embodiments, process 900 may be executed by the RT system 100. For example, the process 900 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 900.

Operations 901-903 may be performed in a similar manner as that of operations 801-803 as described in connection with FIG. 8, and the descriptions thereof are not repeated here.

In 904, the processing device 140 (e.g., the fluence map determination module 440) (e.g., the processing circuits of the processor 210) may determine the fluence map corresponding to the radiation field based on the EPID image corresponding to the radiation field. In some embodiments, operation 904 may include operation 904A and 904B. In 904A, the processing device 140 may obtain the EPID image corresponding to the radiation field from an auxiliary device (e.g., an EPID) of the RT device and perform a pre-processing (e.g., a denoising processing, a grayscale transformation, a geometric transformation, an image enhancement) on the EPID image. In 904B, the processing device 140 may perform a digital image processing (e.g., an image binarization operation) on the EPID image.

Operations 905-911 may be performed in a manner similar to that of operations 807-813 as described in connection with FIG. 8, and the descriptions thereof are not repeated here.

In some embodiments, the operation 806 as described in FIG. 8 may be performed in a same manner as that of operations 904. In some embodiments, in the operation 806, at least one of operations of a de-scattering or an image back-projection may be further performed on the EPID image corresponding to the radiation field to determine the fluence map corresponding to the radiation field, which may improve the accuracy of the determined fluence map.

It should be noted that the above description regarding the process 900 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 900 may be accomplished with one or more additional operations not described and/or without one or more of the operations discussed above.

EXAMPLES

The following examples are provided for illustration purposes and not intended to be limiting.

FIG. 10A is a schematic diagram illustrating an ideal fluence image. FIG. 10B is a schematic diagram illustrating a fluence image reconstructed based on a Wiener filter deconvolution. FIG. 10C is a schematic diagram illustrating a fluence image reconstructed based on an iterative deconvolution. For a specific radiotherapy plan, an ideal fluence map may refer to a fluence map in which information, such as a target region, radiation doses corresponding to the target region, etc., is consistent with the corresponding information in the radiotherapy plan. The fluence map shown in FIG. 10B was obtained by performing a pre-processing, a de-scattering in a Monte Carlo manner, a Wiener filter deconvolution, and a digital image processing on an EPID image obtained based on the radiotherapy plan. The fluence map shown in FIG. 10C was obtained by performing the pre-processing, the de-scattering by a Monte Carlo simulation, an iterative deconvolution, and the digital image processing on the EPID image, respectively. FIG. 10D is a schematic diagram illustrating horizontal numerical comparison curves corresponding to the fluence images in FIGS. 10A-10C. FIG. 10E is a schematic diagram illustrating longitudinal numerical comparison curves corresponding to the fluence images in the FIGS. 10A-10C. By comparing the three fluence maps shown in FIG. 10A-10C, three horizontal numerical comparison curves shown in FIG. 10D, and three longitudinal numerical comparison curves shown in FIG. 10E, the fluence map shown in FIG. 10B and the fluence map shown in FIG. 10C are similar, the fluence map shown in FIG. 10B and the fluence map shown in FIG. 10C have certain errors compared with the ideal fluence map.

FIGS. 11A-11H are schematic diagrams illustrating 8 fluence images reconstructed based on 8 radiation tasks corresponding to a radiotherapy plan according to some embodiments of the present disclosure. According to a specific radiotherapy plan, 8 radiation tasks were obtained. For each of the 8 radiation tasks, a fluence image corresponding to the radiation task was obtained by performing the pre-processing, the de-scattering by a Monte Carlo simulation, and the digital image processing on an EPID image corresponding to the radiation task. That is, the 8 fluence images were reconstructed according to methods described in the present disclosure.

Figure 12A:
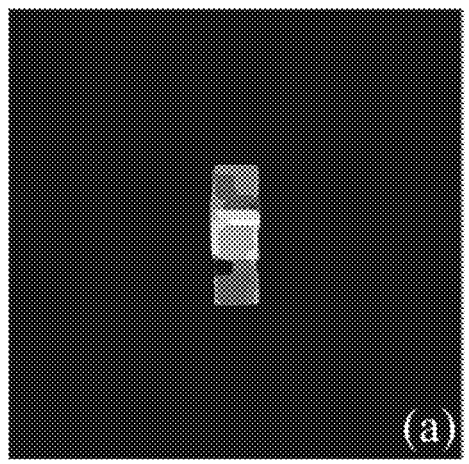
FIG. 12A is a schematic diagram illustrating a target fluence image obtained based on 8 fluence images in the FIGS. 11A-11H.
Figure 12B:
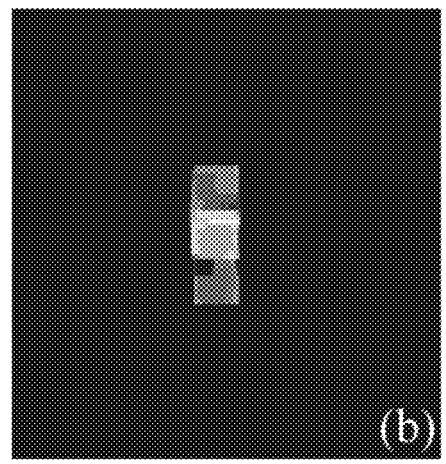
FIG. 12B is a schematic diagram illustrating an ideal fluence image.

FIG. 12A is a schematic diagram illustrating a target fluence image obtained based on the 8 fluence images in the FIGS. 11A-11H. The target fluence image shown in FIG. 12A was determined by combining the 8 fluence images shown in the FIGS. 11A-11H. FIG. 12B is a schematic diagram illustrating an ideal fluence image corresponding to the radiotherapy plan as described in connection with FIGS. 11A-11H. By comparison, the target fluence image shown in FIG. 12A and the ideal fluence image shown in FIG. 12B are similar.

Figure 12C:
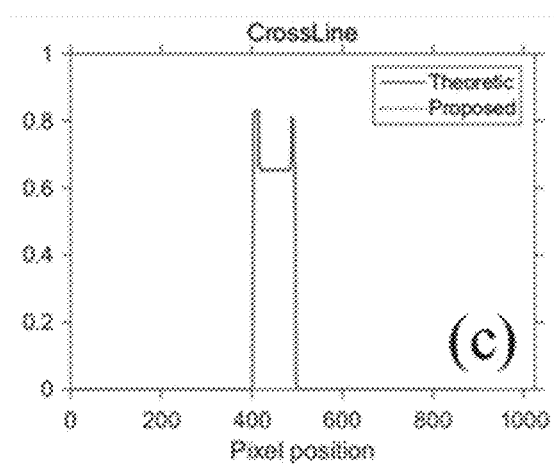
FIG. 12C is a schematic diagram illustrating horizontal numerical comparison curves corresponding to a target fluence image in the FIG. 12A and an ideal fluence image in the FIG. 12B, respectively.
Figure 12D:
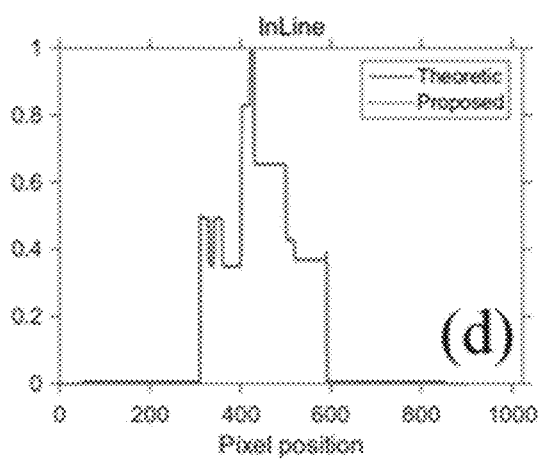
FIG. 12D is a schematic diagram illustrating longitudinal numerical comparison curves corresponding to a target fluence image in the FIG. 12A and an ideal fluence image in the FIG. 12B, respectively.

FIG. 12C is a schematic diagram illustrating horizontal numerical comparison curves corresponding to the target fluence image in the FIG. 12A and the ideal fluence image in the FIG. 12B. By comparison, except for a few pixel positions, the horizontal numerical comparison curve corresponding to the target fluence image substantially overlaps the horizontal numerical comparison curve corresponding to the ideal fluence image. FIG. 12D is a schematic diagram illustrating longitudinal numerical comparison curves corresponding to the target fluence image in the FIG. 12A and the ideal fluence image in the FIG. 12B. By comparison, except for a few pixel positions, the longitudinal numerical comparison curve corresponding to the target fluence image substantially overlaps the longitudinal numerical comparison curve corresponding to the ideal fluence image. The substantial overlap of the above curves indicates that the target fluence image reconstructed according to the methods described in the present disclosure is similar to the ideal fluence image. Therefore, the methods described in the present disclosure can improve the accuracy of the reconstructed fluence map.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local region network (LAN) or a wide region network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for reconstructing a fluence map, comprising:
   at least one storage device including a set of instructions; and
   at least one processor in communication with the at least one storage device, wherein when executing the set of instructions, the at least one processor is directed to perform operations including:
   obtaining a plurality of radiation tasks based on a radiotherapy plan, each radiation task of the plurality of radiation tasks including a radiation field corresponding to the each radiation task;
   for the each radiation task of the plurality of radiation tasks,
      determining whether a radiation field shape change between the radiation field corresponding to the each radiation task and a radiation field corresponding to a preceding radiation task exceeds a shape change threshold; and
      determining a fluence map corresponding to the each radiation task based on a first determination result of whether the radiation field shape change between the radiation field corresponding to the each radiation task and the radiation field corresponding to the preceding radiation task exceeds the shape change threshold.

2. The system of claim 1, wherein:
   the first determination result includes that the radiation field shape change exceeds the shape change threshold; and the determining the fluence map corresponding to the each radiation task based on the first determination result includes updating the fluence map corresponding to the each radiation task.

3. The system of claim 2, wherein the updating the fluence map corresponding to the each radiation task comprises:
determining whether a movement change of the radiation field corresponding to the each radiation task during an execution process of the each radiation task exceeds a movement change threshold; and
determining the fluence map corresponding to the each radiation task based on a second determination result of whether the movement change of the radiation field corresponding to the each radiation task exceeds the movement change threshold.

4. The system of claim 3, wherein:
the second determination result includes that the movement change exceeds the movement change threshold;
the determining the fluence map corresponding to the each radiation task based on the second determination result includes:
determining a plurality of radiation sub-tasks based on the movement change threshold; and
determining the fluence map corresponding to the each radiation task based on the plurality of radiation sub-tasks.

5. The system of claim 4, wherein:
a change of radiation sub-fields corresponding to two neighboring radiation sub-tasks is within the movement change threshold; or
for each of the plurality of radiation sub-tasks, a change of a radiation sub-field corresponding to the radiation sub-task during an execution process of the radiation sub-task is within the movement change threshold.

6. The system of claim 5, wherein the determining the fluence map corresponding to the each radiation task based on the plurality of radiation sub-tasks comprises:
for each of the plurality of radiation sub-tasks, determining a fluence sub-map corresponding to the radiation sub-task; and
determining the fluence map corresponding to the each radiation task by combining a plurality of fluence sub-maps corresponding to the plurality of radiation sub-tasks.

7. The system of claim 6, wherein for each of the plurality of radiation sub-tasks, the determining the fluence sub-map corresponding to the radiation sub-task comprises:
obtaining an electronic portal imaging device (EPID) image corresponding to the radiation sub-task; and
determining the fluence sub-map corresponding to the radiation sub-task based on the EPID image corresponding to the radiation sub-task.

8. The system of claim 2, the updating the fluence map corresponding to the each radiation task comprises:
obtaining an EPID image corresponding to the each radiation task; and
determining the fluence map corresponding to the each radiation task by converting the EPID image corresponding to the each radiation task.

9. The system of claim 1, wherein:
the first determination result includes that the radiation field shape change is less than the shape change threshold; and
the determining the fluence map corresponding to the each radiation task based on the first determination result includes designating a fluence map corresponding to the preceding radiation task as the fluence map corresponding to the each radiation task.

10. The system of claim 1, further comprising:
determining a target fluence map by combining a plurality of fluence maps corresponding to the plurality of radiation tasks.

11. The system of claim 1, wherein the radiation field is formed by a plurality of leaves or jaw blades of a collimator at different positions and the radiation field shape change includes a movement of at least one of the plurality of leaves or jaw blades.

12. A system for reconstructing a fluence map, comprising:
at least one storage device including a set of instructions; and
at least one processor in communication with the at least one storage device, wherein when executing the set of instructions, the at least one processor is directed to perform operations including:
obtaining a plurality of radiation tasks based on a radiotherapy plan, each radiation task of the plurality of radiation tasks including a radiation field corresponding to the each radiation task;
for each radiation task of the plurality of radiation tasks,
determining whether a movement change of the radiation field corresponding to the each radiation task during an execution process of the each radiation task exceeds a movement change threshold; and
determining a fluence map corresponding to the each radiation task based on the determination of whether the movement change of the radiation field corresponding to the each radiation task exceeds the movement change threshold.

13. The system of claim 12, wherein:
the determination of whether the movement change of the radiation field corresponding to the each radiation task exceeds the movement change threshold includes that the movement change exceeds the movement change threshold;
the determining the fluence map corresponding to the each radiation task based on the determination of whether the movement change of the radiation field corresponding to the each radiation task exceeds the movement change threshold includes:
determining a plurality of radiation sub-tasks based on the movement change threshold; and
determining the fluence map corresponding to the each radiation task based on the plurality of radiation sub-tasks.

14. The system of claim 13, wherein:
a change of radiation sub-fields corresponding to two neighboring radiation sub-tasks is within the movement change threshold; or
for each of the plurality of radiation sub-tasks, a change of a radiation sub-field corresponding to the radiation sub-task during an execution process of the radiation sub-task is within the movement change threshold.

15. The system of claim 14, wherein the determining the fluence map corresponding to the each radiation task based on the plurality of radiation sub-tasks comprises:
for each of the plurality of radiation sub-tasks, determining a fluence sub-map corresponding to the radiation sub-task; and determining the fluence map corresponding to the each radiation task by combining a plurality of fluence sub-maps corresponding to the plurality of radiation sub-tasks.

16. The system of claim 15, wherein for each of the plurality of radiation sub-tasks, the determining the fluence sub-map corresponding to the radiation sub-task comprises:
obtaining an electronic portal imaging device (EPID) image corresponding to the radiation sub-task; and
determining the fluence sub-map corresponding to the radiation sub-task based on the EPID image corresponding to the radiation sub-task.

17. A method for reconstructing a fluence map, the method being implemented on a computing device including at least one processor and at least one storage device, the method comprising:
obtaining a plurality of radiation tasks based on a radiotherapy plan, each radiation task of the plurality of radiation tasks including a radiation field corresponding to the each radiation task;
for each radiation task of the plurality of radiation tasks,
determining whether a radiation field shape change between the radiation field corresponding to the each radiation task and a radiation field corresponding to a preceding radiation task exceeds a shape change threshold; and
determining a fluence map corresponding to the each radiation task based on a first determination result of whether the radiation field shape change between the radiation field corresponding to the each radiation task and the radiation field corresponding to the preceding radiation task exceeds the shape change threshold.

18. The method of claim 17, wherein:
the first determination result includes that the radiation field shape change exceeds the shape change threshold; and
the determining the fluence map corresponding to the each radiation task based on the first determination result includes updating the fluence map corresponding to the each radiation task.

19. The method of claim 18, the updating the fluence map corresponding to the each radiation task comprises:
obtaining an EPID image corresponding to the each radiation task; and
determining the fluence map corresponding to the each radiation task by converting the EPID image corresponding to the each radiation task.

20. The method of claim 17, wherein:
the first determination result includes that the radiation field shape change is less than the shape change threshold; and
the determining the fluence map corresponding to the each radiation task based on the first determination result includes designating a fluence map corresponding to the preceding radiation task as the fluence map corresponding to the each radiation task.

* * * * *